United States Patent
Ben-Haim

(10) Patent No.: US 6,983,179 B2
(45) Date of Patent: Jan. 3, 2006

(54) METHOD FOR MAPPING A HEART USING CATHETERS HAVING ULTRASONIC POSITION SENSORS

(75) Inventor: Shlomo Ben-Haim, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/783,150

(22) Filed: Feb. 14, 2001

(65) Prior Publication Data

US 2002/0045810 A1    Apr. 18, 2002

Related U.S. Application Data

(60) Continuation of application No. 09/111,317, filed on Jul. 7, 1998, now Pat. No. 6,285,898, which is a continuation-in-part of application No. 08/595,365, filed on Feb. 1, 1996, now Pat. No. 5,738,096, and a continuation-in-part of application No. 08/311,593, filed on Sep. 23, 1994, now Pat. No. 5,546,951, which is a division of application No. 08/094,539, filed on Jul. 20, 1993, now Pat. No. 5,391,199.

(60) Provisional application No. 60/009,769, filed on Jan. 11, 1996.

(51) Int. Cl.
*A61B 5/05* (2006.01)

(52) U.S. Cl. ................... 600/374; 600/424; 600/508

(58) Field of Classification Search ............ 600/424, 600/425, 426, 427, 450, 466, 459, 374, 378, 600/508, 509, 413, 527; 607/122

See application file for complete search history.

(56) References Cited

U.S. PATENT DOCUMENTS

| | | | |
|---|---|---|---|
| 4,917,095 A | 4/1990 | Fry et al. | |
| 4,921,482 A | 5/1990 | Hammerslag et al. | |
| 5,195,968 A | 3/1993 | Lundquist et al. | |
| 5,211,165 A | 5/1993 | Dumoulin et al. | |
| 5,222,501 A | 6/1993 | Ideker et al. | |
| 5,279,309 A | 1/1994 | Taylor et al. | |
| 5,285,788 A | 2/1994 | Arenson et al. | |
| 5,368,564 A | 11/1994 | Savage | |
| 5,368,592 A | 11/1994 | Stern et al. | |
| 5,373,849 A | 12/1994 | Maroney et al. | |
| 5,383,923 A | 1/1995 | Webster, Jr. | |
| 5,391,199 A | 2/1995 | Ben-Haim | |
| 5,403,356 A | 4/1995 | Hill et al. | |
| 5,404,297 A | 4/1995 | Birk et al. | |
| 5,409,000 A * | 4/1995 | Imran ..................... | 600/424 |
| 5,431,168 A | 7/1995 | Webster, Jr. | |
| 5,433,198 A | 7/1995 | Desai | |
| 5,443,489 A | 8/1995 | Ben-Haim | |
| 5,450,846 A | 9/1995 | Goldreyer | |
| 5,465,717 A | 11/1995 | Imran et al. | |
| 5,471,982 A | 12/1995 | Edwards et al. | |

(Continued)

FOREIGN PATENT DOCUMENTS

WO    95/05733 A1    3/1995

(Continued)

*Primary Examiner*—Lee S. Cohen
(74) *Attorney, Agent, or Firm*—Ladas & Parry LLP

(57) ABSTRACT

A method for mapping a heart comprises the steps of inserting a mapping catheter having an ultrasonic position sensor into the heart. At least one reference catheter having an ultrasonic position sensor is also inserted into the heart. The position of the mapping catheter is determined relative to the at least one reference catheter and a portion of the heart is mapped with the mapping catheter. Additionally, the at least one reference catheter may be provided outside of the heart.

28 Claims, 14 Drawing Sheets

U.S. PATENT DOCUMENTS

| | | |
|---|---|---|
| 5,487,391 A | 1/1996 | Panescu |
| 5,515,853 A | 5/1996 | Smith et al. |
| 5,555,883 A | 9/1996 | Avitall |
| 5,558,091 A | 9/1996 | Acker et al. |
| 5,558,092 A | 9/1996 | Unger et al. |
| 5,577,502 A | 11/1996 | Darrow et al. |
| 5,588,432 A | 12/1996 | Crowley |
| 5,592,939 A | 1/1997 | Martinelli |
| 5,601,084 A | 2/1997 | Sheehan et al. |
| 5,738,096 A | 4/1998 | Ben-Haim |
| 5,779,638 A | 7/1998 | Vesely et al. |
| 5,795,298 A | 8/1998 | Vesely et al. |
| 5,797,849 A | 8/1998 | Vesely et al. |
| 5,817,022 A | 10/1998 | Vesely |
| 5,830,144 A | 11/1998 | Vesely |
| 5,868,673 A | 2/1999 | Vesely |
| 5,954,649 A * | 9/1999 | Chia et al. ............ 600/424 |
| 6,070,094 A * | 5/2000 | Swanson et al. ........... 600/374 |
| 6,216,027 B1 * | 4/2001 | Willis et al. ............ 600/424 |
| 6,221,013 B1 * | 4/2001 | Panescu et al. ........... 600/437 |

FOREIGN PATENT DOCUMENTS

| | | |
|---|---|---|
| WO | 95/07657 A1 | 3/1995 |
| WO | 95/10226 A1 | 4/1995 |
| WO | 95/19738 A1 | 7/1995 |
| WO | 96/05768 A1 | 2/1996 |
| WO | 97/24981 A2 | 7/1997 |
| WO | 99/05971 A1 | 2/1999 |
| WO | 00/07501 A1 | 2/2000 |

* cited by examiner

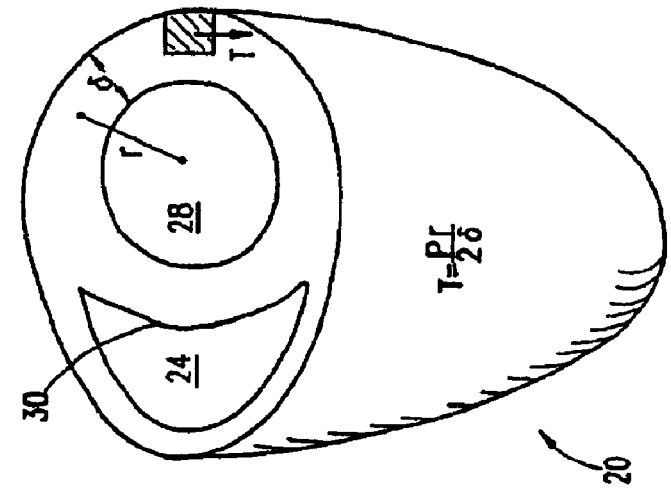
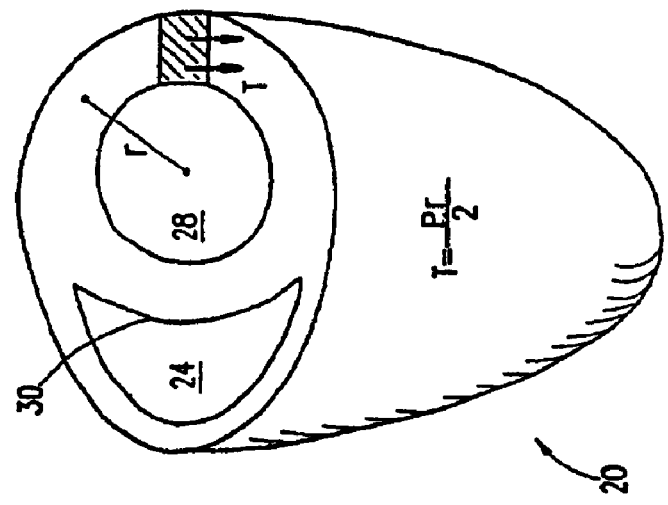
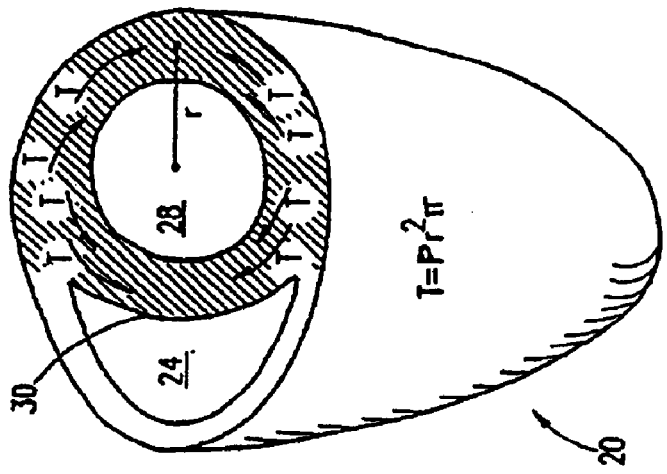

METHOD FOR MAPPING A HEART USING CATHETERS HAVING ULTRASONIC POSITION SENSORS

FIELD OF THE INVENTION

This is a Continuation of U.S. patent application Ser. No. 09/111,317, filed on Jul. 7, 1998, now issued U.S. Pat. No. 6,285,898, which is a Continuation-in-Part of U.S. patent application Ser. No. 08/595,365, filed on Feb. 1, 1996, now issued U.S. Pat. No. 5,738,096, which claims the benefit of U.S. Provisional Patent Application No. 60/009,769, filed on Jan. 11, 1996, and is a Continuation-in-Part of U.S. patent application Ser. No. 08/311,593, filed on Sep. 23, 1994, now issued U.S. Pat. No. 5,546,951, which is a Division of U.S. patent application Ser. No. 08/094,539, filed on Jul. 20, 1993, now issued U.S. Pat. No. 5,391,199.

BACKGROUND OF THE INVENTION

Cardiovascular diseases accounted for approximately 43 percent of the mortality in the United States of America in 1991 (923,000 persons). However, many of these deaths are not directly caused by an acute myocardial infraction (AMI). Rather, many patients suffer a general decline in their cardiac output known as heart failure. Once the overt signs of heart failure appear, half the patients die within five years. It is estimated that between two and three million Americans suffer from heart failure and an estimated 200,000 new cases appear every year. In many cases heart failure is caused by damage accumulated in the patient's heart, such as damage caused by disease, chronic and acute ischemia and especially (~75%) as a result of hypertension.

A short discussion of the operation of a healthy heart is usefull in order to appreciate the complexity of the functioning of the heart and the multitude of pathologies which can cause heart failure. FIG. 1A is a schematic drawing of a cross-section of a healthy heart 20. In general heart 20 comprises two independent pumps. One pump comprises a right atrium 22 and a right ventricle 24 which pump venous blood from an inferior and a superior vena cava to a pair of lungs (not shown) to be oxygenated. Another pump comprises a left atrium 26 and a left ventricle 28, which pump blood from pulmonary veins (not shown) to a plurality of body systems, including heart 20 itself. The two ventricles are separated by a ventricular septum 30 and the two atria are separated by an atrial septum 32.

Heart 20 has a four phase operational cycle in which the two pumps are activated synchronously. FIG. 1B shows a first phase, called systolic. During this phase, right ventricle 24 contracts and ejects blood through a pulmonic valve 34 to the lungs. At the same time, left ventricle 28 contracts and ejects blood through an aortic valve 36 and into an aorta 38. Right atrium 22 and left atrium 26 are relaxed at this point and they begin filling with blood, however, this preliminary filling is limited by distortion of the atria which is caused by the contraction of the ventricles.

FIG. 1C shows a second phase, called rapid filling phase and indicates the start of a diastole. During this phase, right ventricle 24 relaxes and fills with blood flowing from right atrium 22 through a tricuspid valve 40, which is open during this phase. Pulmonic valve 34 is closed, so that no blood leaves right ventricle 24 during this phase. Left ventricle 28 also relaxes and is filled with blood flowing from left atrium 26 through a mitral valve 42, which is open. Aortic valve 36 is also closed to prevent blood from leaving left ventricle 26 during this phase. The filling of the two ventricles during this phase is affected by an existing venous pressure. Right atrium 22 and left atrium 26 also begin filling during this phase. However, due to relaxation of the ventricles, their pressure is lower than the pressure in the atria, so tricuspid valve 40 and mitral valve 42 stay open and blood flows from the atria into the ventricles.

FIG. 1D shows a third phase called diastatis, which indicates the middle of the diastole. During this phase, the ventricles fill very slowly. The slowdown in filling rate is due to the equalization of pressure between the venous pressure and the intra-cardiac pressure. In addition, the pressure gradient between the atria and the ventricles is also reduced.

FIG. 1E shows a fourth phase called atrial systole which indicates the end of the diastole and the start of the systole of the atria During this phase, the atria contract and inject blood into the ventricles. Although there are no valves guarding the veins entering the atria, there are some mechanisms to prevent backflow during atrial systole. In left atrium 26, sleeves of atrial muscle extend for one or two centimeters along the pulmonary veins and tend to exert a sphincter-like effect on the veins. In right atrium 22, a crescentic valve forms a rudimentary valve called the eustachian valve which covers the inferior vena cava. In addition, there may be muscular bands which surround the vena cava veins at their entrance to right atria 22.

FIG. 1F is graph showing the volume of left ventricle 24 as a function of the cardiac cycle. FIG. 1F clearly shows the additional volume of blood injected into the ventricles by the atria during atrial systole as well as the variance of the heart volume during a normal cardiac cycle. FIG. 1G is a graph which shows the time derivative of FIG. 1F, i.e., the left ventricle fill rate as a function of cardiac cycle. In FIG. 1G two peak fill rates are shown, one in the beginning of diastole and the other during atrial systole.

An important timing consideration in the cardiac cycle is that the atrial systole must complete before the ventricular systole begins. If there is an overlap between the atrial and ventricular systoles, the atria will have to force blood into the ventricle against a raising pressure, which reduces the volume of injected blood. In some pathological and induced cases, described below, the atrial systole is not synchronized to the ventricular systole, with the effect of a lower than optimal cardiac output.

It should be noted that even though the left and the right sides of heart 20 operate in synchronization with each other, their phases do not exactly overlap. In general, right atrial systole starts slightly before left atrial systole and left ventricular systole starts slightly before right ventricular systole. Moreover, the injection of blood from left ventricle 26 into aorta 38 usually begins slightly after the start of injection of blood from right ventricle 24 towards the lungs and ends slightly before end of injection of blood from right ventricle 24. This is caused by pressures differences between the pulmonary and body circulatory systems.

When heart 20 contracts (during systole), the ventricle does not contract in a linear fashion, such as shortening of one dimension or in a radial fashion. Rather, the change in the shape of the ventricle is progressive along its length and involves a twisting effect which tends to squeeze out more blood. FIG. 2 shows an arrangement of a plurality of muscle fibers 44 around left ventricle 28 which enables this type of contraction. When muscle fibers 44 are arranged in a spiral manner as shown in FIG. 2 and the activation of muscle fibers 44 is started from an apex 46 of left ventricle 28, left ventricle 28 is progressively reduced in volume from the bottom up. The spiral arrangement of muscle fibers 44 is important because muscle fibers typically contract no more than 50% in length. A spiral arrangement results in a greater change of left ventricular volume than is possible with, for example, a flat arrangement in which the fibers are arranged in bands around the heart. An additional benefit of the spiral arrangement is a leverage effect. In a flat arrangement, a contraction of 10% of a muscle fiber translates into a reduction of 10% of the ventricular radius. In a spiral arrangement with, for example, a spiral angle 48 of 45°, a 10% contraction translates into a 7.07% contraction in ventricular radius and a 7.07% reduction in ventricular length, Since the ventricular radius is typically smaller than the ventricular length, the net result is that, depending on spiral angle 48, a tradeoff is effected between a given amount of contraction and the amount of force exerted by that contraction.

Spiral angle 48 is not constant, rather, spiral angle 48 changes with the distance of a muscle fiber from the outer wall of the ventricle. The amount of force produced by a muscle fiber is a function of its contraction, thus, each layer is optimized to produce an optimal amount of force. Since the contraction of each muscle fiber is synchronous with the increase in the ventricular pressure (caused by the muscle contraction), it might be expected that the muscle fibers produce a maximum force at maximum contraction. However, physiological constraints on muscle fibers denote that maximal force is generated before maximal contraction. In addition, the force exerted by a muscle fiber begins to fall soon after maximum force is exerted. The varying spiral angle is a mechanism which makes it possible to increase the contractile force on the ventricle after maximum force is reached by a particular muscle fiber.

As described above, activation of the heart muscle is from the apex up. Thus, the muscle on the top of the ventricle could theoretically exert more force than the muscle at apex 46, which would cause a distention at apex 46. The varying spiral angle is one mechanism to avoid distention. Another mechanism is that the muscle near apex 46, which is activated first, is slightly more developed than the muscle at the top of the ventricle, which is activated last. As a result of the above described mechanisms, the force exerted by the ventricular wall is more evenly distributed over time and space. It should be appreciated that blood which remains in one place without moving, even in the heart, can clot, so it is very important to eject as much blood as possible out of the heart.

As can be appreciated, a complicated mechanism is required to synchronize the activation of muscle fibers 44 so that an efficient four phase cycle is achieved. This synchronization mechanism is provided by an electrical conduction system within the heart which conducts an electrical activation signal from a (natural) cardiac pacemaker to muscle fibers 44.

FIG. 3 shows the main conduction pathways in heart 20. An SA node 50, located in right atrium 22, generates an activation signal for initiating contraction of muscle fibers 44. The activation signal is transmitted along a conduction pathway 54 to left atria 26 where the activation signal is locally disseminated via Bachman bundles and Crista terminals. The activation signal for contracting the left and right ventricles is conducted from SA node 50 to an AV node 52, where the activation signal is delayed. The ventricles are normally electrically insulated from the atria by non-conducting fibrous tissue, so the activation signal must travel through special conduction pathways. A left ventricle activation signal travels along a left pathway 58 to activate left ventricle 28 and a right ventricle activation signal travels along a right pathway 56 to activate right ventricle 24. Generally, the conduction pathways convey the activation signal to apex 46 where they are locally disseminated via Purkinje fibers 60 and propagation over the rest of the heart is achieved by conduction in muscle fibers 44. In general, the activation of the heart is from the inner surface towards the outer surface. It should be noted that electrical conduction in muscle fibers 44 is generally faster along the direction of the muscle fibers. Thus, the conduction velocity of the activation signals in heart 20 is generally anisotropic.

As can be appreciated, the delay in AV node 52 results, in a healthy heart, in proper ventricular systolic sequencing. The temporal distribution of the activation signal in the ventricular muscle results in the activation of the ventricles from the apex up. In a healthy heart the activation signal propagates across left ventricle 28 in approximately 60 milliseconds. In an externally paced heart, where the activation signal is not conducted through Purkinje fibers 60 or in a diseased heart, the propagation time is typically longer, such as 150 milliseconds. Thus, disease and external pacing affect the activation profile of the heart.

Cardiac muscle cells usually exhibit a binary reaction to an activation signal; either the cell responds normally to the activation signal or it does not respond at all. FIG. 4 is a graph showing changes in the voltage of a single cardiac muscle cell in reaction to the activation signal. The reaction is generally divided into five stages. A rapid depolarization stage 62 occurs when the muscle cell receives an activation signal. During this stage, which lasts a few milliseconds, the potential of the cell becomes rapidly positive. After depolarization, the muscle fiber rapidly repolarizes during a rapid repolarization stage 64 until the cell voltage is approximately zero. During a slow repolarization stage 66, also known as the plateau, the muscle cell contracts. The duration of stage 66, the plateau duration, is directly related to the amount of work performed by the muscle cell. A relatively fast repolarization stage 68 follows, where the muscle cell repolarizes to its original potential. Stage 66 is also known as the refractory period, during which the cell cannot be activated by another activation signal. During stage 68, the cell is in a relative refractory period, during which the cell can be activated by an exceptionally strong activation signal. A steady state 70 follows in which the muscle cell is ready for another activation.

It should be appreciated that the contraction of cardiac muscle cells is delayed in time from their activation. In addition the duration of the contraction is generally equal to the duration of the plateau.

An important factor which may affect the length of the plateau is the existence of an ionic current resulting from the voltage potentials generated by the local depolarizations. The ionic current starts at the last activated portion of the heart and progresses back along the path of the activation. Thus, it is the later activated portions of the heart which are first affected by the ionic current. As a result, the repolarization of these cells is relatively faster than the repolarization of the first activated muscle fibers, and their contraction time is relatively shorter. As can be appreciated, in a healthy heart, where the propagation time of the activation signal is relatively short, the ionic currents are significantly smaller than in a diseased or externally paced heart.

One of the main results of the contraction of the ventricles is increased intra-ventricular pressure. In general, when the intra-cardiac pressure is higher, the outflow from the heart into the circulatory system is stronger and the efficiency of the heart is higher. A mathematical relationship termed Laplace's law can be used to model the relationship between the pressure in the ventricle and the tension in the wall of the ventricle. Laplace's law was formulated for generally spherical or cylindrical chambers with a distentible wall, however, the law can be applied to the ventricles since they are generally elongated spherical in shape. FIGS. 5A–C show three formulations for determining the tension in a portion of the ventricle wall, all of which are based of the law of Laplace. In FIG. 5A, the tension across a cross-section of the wall is shown wherein T, the tension in the wall, is equal to the product of P, the transmural pressure across the wall, r (squared), the radius of the ventricle, and π. FIGS. 5B and C show formulas for calculating the tension per unit in portions of the ventricular wall, for example in FIG. 5C, for a unit cross-sectional area of muscle in a wall of thickness δ.

As can be appreciated, if r, the radius of the ventricle, is large, a higher tension is needed to produce the same pressure change as in a ventricle with a smaller radius. This is one of the reasons that ventricular dilation usually leads to heart failure. The heart muscle is required to produce a higher tension is order to achieve the same pressure gradient. However, the heart is not capable of producing the required tension, so, the pressure gradient, and thus the cardiac efficiency, are reduced.

Unfortunately, not all people have healthy hearts and vascular systems. Some types of heart problems are caused by disease. HCM (hypertrophic cardiomyopathy or HOCM) is a disease in which the left ventricle and, in particular, the ventricular septum, hypertrophy, sometimes to an extent which blocks the aortic exit from the left ventricle. Other diseases, such as atrophy causing diseases, reduce the amount of muscle fibers in portions of the heart.

A very common cause of damage to the heart is ischemia of the heart muscle. This condition, especially when manifesting itself as an acute myocardial infraction (heart attack), can create dead zones in the heart which do not contain active muscle. An additional, and possibly more important effect, is the non-conducting nature of these dead zones which may upset the natural activation sequence of the heart. In some cases, damaged heart tissue continues to conduct the activation signal, albeit at a variable or lower velocity, which may cause arrhythmias.

A chronic ischemic condition is usually caused by blockage of the coronary arteries, usually by arteriosclerosis, which limits the amount of oxygen which can reach portions of the heart muscle. When more work (i.e., more tension) is required of the heart muscle and an increase in oxygen supply is not available, the result is acute pain, and if the supply is cut off for an extended period, death of the starved muscle will follow.

When the output of the heart is insufficient, a common result is hypertrophy of the heart, usually of the left ventricle. Hypertrophy is a compensatory mechanism of the heart for increasing the output volume. However, in a chronic condition, hypertrophy has generally negative effects. For example, arrhythmias, congestive heart failure (CHF) and permanent changes in the morphology of the heart muscle (ventricular modeling) may result from hypertrophy.

One of the most common cardiovascular diseases is hypertension. A main effect of hypertension is increased cardiac output demand, which causes hypertrophy since the blood must be pumped against a higher pressure. Furthermore, hypertension usually aggravates other existing cardiac problems.

The human heart has many compensatory and adaptive mechanisms, termed cardiac reserve, so that not all cardiac pathologies manifest as heart disease. Once the cardiac reserve is used up, the heart cannot keep up with the demand and heart failure may result. One measure of heart function and efficiency is the left ventricle ejection factor, which is the ratio between the amount of blood in the left ventricle during diastole and the amount of blood exiting during systole. It should be noted that a significant portion of the change in ventricular volume between systole and diastole is due to the thickening of activated muscle fibers. Another measure of heart function is the left ventricle stroke volume, which is the amount of blood which is ejected from the left ventricle each heart beat. It should be noted that once the cardiac reserve is used up it is difficult, if not impossible, for the heart to increase its output when needed, such as during exercise.

There are many-ways in which non-optimal timing of the activation of the heart can result in lower cardiac output. In AF (atrial fibrillation) one or both atria does not contract in correct sequence with its associated ventricle. As a first result, the atria does not inject blood into its associated ventricle during atrial systole, so the ventricle volume is not maximized before ventricular systole, and stroke volume is slightly reduced. If the right atria is fibrillating, sequencing of the AV node is non-regular, which results in the ventricles contracting at an irregular rate, and the heart output is further reduced.

In some cases of a conduction block between the SA node and the ventricles, such as caused by a damaged AV node, the contraction of the atria is not synchronized to the contraction of the ventricles, which also results in a lower heart output.

Another type of timing deficiency results when there are large dead areas in the heart muscle which do not conduct electrical signals. The activation signal must circumvent the dead areas, which results in a longer pathway (and longer delay time) for the activation signal reaching some portions of the heart. In some cases, these portions of the heart are activated long after the rest of the heart has already contracted, which results in a reduced contribution of these portions to the total cardiac output.

Heart muscle which is stressed before it is activated, heart muscle which is weakened (such as by ischemia) and portions of the heart which have turned into scar tissue, may form aneurysms. As can be appreciated from Laplace's law, portions of the ventricle wall which do not generate enough tension to offset the tension induced by the intra-cardiac pressure must increase their local radius in response to the pressure overload. The stretched wall portion thins out and may burst, resulting in the death of the patient. The apex of the left ventricle is especially susceptible to aneurysms since it may be very thin. In addition, the total pressure in the ventricle and the flow from the ventricle are reduced as the aneurysm grows, so the heart output is also reduced. Although weak muscle should be expected to hypertrophy in response to the greater need, in some cases, such as after an AMI, hypertrophy may not occur before irreversible tissue changes are caused by the stretching.

Perfusion of the heart muscle usually occurs during diastole. However, if the diastole is very long, such as when the activation signal is propagated slowly, some portions of the heart may not be oxygenated properly, resulting in functional ischemia.

As mentioned above, one of the adaptation mechanisms of the heart is hypertrophy, in which the size of the heart increases to answer increased demand. However, hypertrophy increases the danger of arrhythmias, which in some cases reduce heart output and in others, such as VF (ventricular fibrillation) are life threatening. Arrhythmias are also caused by damaged heart tissues which generate erroneous activation signals and by blocks in the conduction system of the heart.

In some cases arrhythmias of the heart are treated using medicines, in others, by implanting a pacemaker or a defibrillator. A common pacemaker implanting procedure, for example for treating the effects of AF, includes:

(a) ablating or removing the AV node; an (b) implanting a pacing electrode in the apex of the heart. The location of the pacing electrode may be changed (during the procedure) if the heart does not beat at a desired sequence for a given output of the pacemaker.

It is also known to pace using multiple electrodes, where the activation signal is initiated from a selected one or more of the electrodes, depending on sensed electrical values, such as sequence, activation time and depolarization state. Typically, the pacing regime is adapted to a specific arrhythmia. Sometimes, logic is included in the pacemaker which enables it to identify and respond to several types of arrhythmia.

U.S. Pat. No. 5,403,356 to Hill et al. describes a method of preventing atrial arrhythmias by adapting the pacing in the right atrium in response to a sensed atrial depolarization, which may indicate an arrhythmia.

Sometimes the pacing is performed for more than one chamber. For example, in dual chamber pacing, both left and right ventricles are separately paced. There have been attempts to use dual chamber pacing to relive aortic obstruction caused by HCM. The aortic exit from the left ventricle is located between the left and right ventricle, so that when both ventricles contract simultaneously, the aorta is squeezed from all sides. In a healthy heart, the ventricular septum does not obstruct the aorta, however, in an HCM-diseased heart, the enlarged septum obstructs the aortic exit from the left ventricle. When pacing to reduce aortic obstruction, the contractions of the left and right ventricles are stepped, so that when the left ventricle contracts, the right ventricle dilates and the aorta is less compressed.

Lameh Fananapazir, Neal D. Epstein, Rodolfo V. Curiel, Julio A. Panza, Dorothy Tripodi and Dorothea McAreavey, in "Long-Term Results Of Dual-Chamber (DDD) Pacing In Obstructive Hypertrophic Cardiomyopathy", *Circulation*, Vol. 90, No. 60, pp. 2731–2742, December 1994, the disclosure of which is incorporated herein by reference, describes the effects of pacing a HCM-diseased heart using DDD pacing at the apex of the right ventricle. One effect is that the muscle mass near the pacing location is reduced, i.e., the ventricular septum is atrophied. The atrophy is hypothesized to be caused by the changes in workload at the paced location which are due to the late activation time of ventricular segments far from the pacing location.

Margarete Hochleitner, Helmut Hortnagl, Heide Hortnagl, Leo Fridrich and Franz Gschnitzer, in "Long-Term Efficiency Of Physiologic Dual-Chamber Pacing In The Treatment Of End-Stage Idiopathic Dilated Cardiomyopathy", *American Journal of Cardiology*, volume 70, pp. 1320–1325, 1992, the disclosure of which is incorporated herein by reference, describes the effect of DDD pacing on hearts which are dilated as a result of idiopathic dilated cardiomyopathy. DDD pacing resulted in an improvement of cardiac function and in a reduction in hypertrophy in several patients. In addition, it is suggested that positioning the ventricular electrode of the DDD pacemaker in near the apex of the right ventricle reduced the stress at the apex of the left ventricle, by its early activation. No method is suggested for choosing the implantation location of the electrodes.

Xavier Jeanrenaud, Jean-Jacques Goy and Lukas Kappenberger, in "Effects Of Dual Chamber Pacing In Hypertrophic Obstructive Cardiomyopathy", *The Lancet*, Vol. 339, pp. 1318–1322, May 30, 1992, the disclosure of which is incorporated herein by reference, teaches that to ensure success of DDD pacing in HCM diseased hearts, an optimum AV interval (between atrial activation and ventricular activation) is required. In addition, it is suggested that this optimal AV interval is modified by performing exercise.

Several methods may be used to treat heart failure. One method is to connect assist pumps to the patient's circulatory system, which assist the heart by circulating the blood. To date, no satisfactory long-term assist pump has been developed. In some cases, a diseased heart is removed and replaced by another human heart. However, this is an expensive, complicated and dangerous operation and too few donor hearts are available. Artificial hearts suffer from the same limitations as assist pumps and, like them, are not yet practical.

Certain types of heart failure, such as those caused by conduction blocks in the AV node or by AF can be helped by the implantation of a pacemaker, as described above.

Some cases of heart failure can be helped by medicines which either strengthen the heart, correct arrhythmias or reduce the total volume of blood in the body (which reduces blood pressure): However, many cases of heart failure can only be treated by reducing the activity of the patient. Ultimately, once the cardiac reserve is used up, most cases of heart failure cannot be treated and result in death.

U.S. Pat. No. 5,391,199, the disclosure of which is incorporated herein by reference, discloses apparatus and method for mapping the electrical activity of the heart. "Biomedical Engineering Handbook", ed. Joseph D. Bronzino, chapter 156.3, pp. 2371–2373, IEEE press/CRC press, 1995, describes modeling strategies in cardiac physiology. On page 2373 a model is described, including experimental support, according to which model the shape of a ventricle is determined by the (local) amount of oxygen consumption. In addition, this model differentiates between pressure overload on the heart, which causes thickening of muscle fibers, denoted concentric hypertrophy, and volume overload which causes an increase in the ventricular volume (by stretching), denoted eccentric hypertrophy. Eccentric hypertrophy may also be caused by reducing the amount of oxygen available to the cardiac muscle.

R. S. Reneman, F. W. Prinzen, E. C. Cheriex, T. Arts and T. Delhass, in "Asymmetrical Changes in Left Ventricular Diastolic Wall Thickness Induced by Chronic Asynchronous Electrical Activation in Man and Dogs", *FASEB J.*, 1993;7; A752 (abstract), abstract number 4341, the disclosure of which in incorporated herein by reference, describe results of studies in paced hearts and which show that earlier activated ventricular wall portions were thinner than later activated wall portions, showing an asymmetrical hypertrophy as a result of the pacing.

C. Daubert, PH. Mabo, Veronique Berder, D. Gras and C. LeClercq, in "Atrial Tachyarrhythmias Associated with High Degree Interatrial Conduction Block: Prevention by Permanent Atrial Resynchronisation", *European Journal of C.P.F*, Vol. 4, No. 1, pp. 35–44, 1994, the disclosure of which is incorporated herein by reference, describes a method of treating atrial fibrillation by implanting pacemaker electrodes in various locations in the heart, including two electrodes in the right atrium.

Frits W. Prinzen, Cornelis H. Augustijn, Theo Arts, Maurits A. Allessie and Robert Reneman, in "Redistribution of Myocardial Fiber Strain and Blood Flow by Asynchronous Activation", *American Journal of Physiology* No. 259 (*Heart Circulation Physiology* No. 28), H300–H308, 1990, the disclosure of which is incorporated herein by reference, describes studies which show that the location of pacing electrodes in a paced heart significantly affect the distribution of strain, and perfusion (blood flow) in the heart.

SUMMARY OF THE INVENTION

It is an object of some aspects of the present invention to provide methods of augmenting the compensatory mechanisms of the heart.

Another object of some aspects of the present invention is to provide methods of mapping the local physiological values and/or the shape of the heart to determine the activation profile of the heart and, preferably, to analyze the resulting maps to determine possible optimizations in the activation profile.

Yet another object of some aspects of the present invention is to control the adaptation mechanisms in the heart so that the heart output or some other parameter of the heart is optimized. Alternatively or additionally, the adaptation mechanisms of the heart are utilized to effect change in the morphology of the heart, such as by redistributing muscle mass.

Still another object of some aspects of the present invention is to control the activation sequence of the heart so that the heart output or some other physiological variable of the heart is optimized, preferably, in real-time.

When used herein, the terms "physiological variable" and "cardiac parameter" do not include electrical activity, rate, arrhythmia or sequencing of the heart. The term "local physiological value" does not include electrical activity, per se, rather it refers to a local physiological state, such as contraction of local heart muscle, perfusion or thickness. The term "location" refers to a location on or in an object, such as the heart muscle. For example, a valve or an apex of the heart. "Position" refers to a position in space, usually relative to a known portion of the heart, for example, 1.5 inches perpendicular from the apex of the heart. The term "local information" includes any information associated with the location on the heart wall, including position and electrical activity.

An object of some aspects of the present invention is related to pacemakers which are adapted to control the adaptation mechanisms of the heart and/or to optimize heart parameters.

In a preferred embodiment of the invention, the mechanical motion of the heart muscle is mapped using a catheter having a position sensor near its distal end. The mapping includes:

(a) placing the catheter into contact with the heart wall;

(b) determining the position of the distal end of the catheter; and (c) repeating step (b) for additional locations in the heart.

Preferably, the catheter is in contact with the heart wall through the entire cardiac cycle. It should be appreciated that contact with the heart wall can be achieved either from the inside or from the outside 6f the heart, such as outside contact being achieved by inserting the catheter into the coronary arteries and/or veins. Alternatively, the catheter is directly inserted into the body (not through the vascular system), such as through a throactoscope or during surgery, Preferably, (b) includes determining the position of the catheter at at least two instants of an entire heart cycle. More preferably, it includes determining the position with time over the cycle. Alternatively or additionally, the catheter has a plurality of distal ends, each with a position sensor and (b) includes determining the position of each one of the ends.

Preferably, the catheter does not move between sequential diastoles. This can be asserted, for example, by using an impedance sensor, by determining changes in a locally sensed electrogram, by determining that the position sensor repeats its trajectory during heart cycles or by determining that the catheter returns to the same location each diastole or other recognizable portion of the cardiac cycle.

Preferably, the mapping further includes determining the geometry and/or changes in the geometry of at least a portion of the heart as a function of time and/or phase of the cardiac cycle. For example, the existence of an aneurysm can be determined from a characteristic bulge of the aneurysm during systole. Likewise, a dilated ventricle can be determined from the determined volume. Additionally or alternatively, the mapping includes determining the local radius of a portion of the heart wall.

Preferably the catheter comprises a pressure sensor which measures the intra-cardiac pressure. Further preferably, the forces on the heart wall are calculated using the local radius and/or the determined pressure, preferably using Laplace's law.

Preferably, the catheter includes at least one electrode for determining the local electrical activity of the heart. Preferably, the local activation time and/or the activation signal is measured and incorporated in a map of the heart. Additionally or alternatively, local electrical conductivity is measured, since fibrous scar tissue does not conduct as well as viable muscle tissue.

A preferred embodiment of the invention provides a map which compares the local activation time to the movement of a segment of local heart wall. Preferably, the map compares activation time of the segment to movement of the segment relative to the movement of surrounding segments. Thus, the reaction of a muscle segment to the activation signal can be determined from the local geometrical changes.

In a preferred embodiment of the invention, the instantaneous thickness of the heart wall at the point of contact is also determined. Preferably, the thickness is measured using an ultrasonic transducer, preferably mounted on the distal portion of the catheter. Preferably, changes in the thickness of the cardiac wall are used to determine the reaction of the heart muscle to the activation signal. Typically, when the muscle contracts, the wall thickens, while if the muscle does not react and the intra-cardiac pressure rises, the wall thins.

In a preferred embodiment of the invention provides a map of the local energy expenditure of the heart. Preferably, the local energy expenditure is determined using Laplace's law, local changes in thickness and a pressure sensor, mounted on the catheter, which determines the intra-cardiac pressure.

In preferred embodiments of the invention, additional or alternative sensors are mounted on the distal end of the catheter and are used in constructing cardiac maps. For example, a Doppler ultrasonic sensor which measures perfusion may be used to determine the local perfusion as a function of time and workload. Additionally or alternatively, an ionic sensor is used to sense changes in ion concentrations.

Although the above maps are described as being time based or cardiac-phase based, in a preferred embodiment of the invention, measurements are binned based on geometrical characteristics of the heart or on ECG or electrogram characteristics. Preferably, the ECG characteristics comprise pulse rate and/or ECG morphology. Maps associated with different bins can be compared to determine pathologies and under utilization of the heart, for example, an abnormal activation profile due to a conduction abnormality, such as a block, for assessing the effects of tachycardia or for assessing changes in the activation profile as a function of heart rate.

Preferably, maps constructed before a cardiac procedure are compared to maps constructed after a procedure to determine the effect of the procedure. In some instances, maps of the heart are constructed while the heart is artificially paced.

A preferred embodiment of the invention provides for changing the distribution of muscle-mass in the heart from an existing muscle-mass distribution to a desired muscle-mass distribution. This is achieved by adjusting the pacing of the heart to achieve an activation profile which affects such change. Preferably, portions of the heart which are relatively atrophied are activated so that relatively more effort is required of them than previously. Alternatively or additionally, portions of the heart which are hypertrophied are activated so that less effort is required of them than previously. Preferably, the decision how to change the activation profile of the heart is based on a map of the heart, further preferably, using a map which shows the local energy expenditure and/or the local work performed by each portion of the heart. Alternatively or additionally, a map which shows the ratio between local perfusion and local energy expenditure is used. Preferably, the activation profile of the heart is changed when the heart approaches the desired muscle mass distribution. Typically, the heart is paced using an implanted pacemaker. Preferably, a map is used to determine the optimal location for the pacing electrode(s). Additionally or alternatively, a treatment course of pharmaceuticals for affecting the activation of the heart, may be designed using such a map and a model of the reaction of the heart to the pharmaceuticals.

Other cardiac treatment options may also be planned and/or decided between using such maps. For example, bypass surgery is only an option if the unperfused tissue (whose ischemia will be relived by the surgery), is viable and its activity (and contribution to the heart) will be improved by the surgery. Thus, before deciding between bypass surgery, PCTA and other reperfusion treatments, it is possible to acquire and analyze a map to help with the decision. In one example, tissue which induces arrhythmia due to ischemia can be detected using a map of the types described herein and a decision to reperfuse made. In another example, performing bypass surgery to increase perfusion to scar tissue, is traumatic to the patient and may actually reduce the perfusion of other parts of the heart. If, before the surgery, a map is consulted, unnecessary surgery may be averted or at least reduced in complexity (double instead of triple bypass)

One aspect of the invention relates to the optimal placement of pacemaker electrodes. A preferred method of determining electrode placement includes:

(a) pacing a heart from a first location;
(b) determining a value of a physiological variable while pacing at the first location;
(c) repeating (a) and (b) at least at a second location; and
(d) implanting the pacing electrode at a location of the first and second locations which yields an optimal value for the physiological variable or at a location with a response known to yield an optimal value in the future.

One preferred physiological variable is the stroke volume. Preferably, the physiological variable is measured using a catheter.

Yet another aspect of the invention relates to pacing a heart to reduce stress. A preferred method of pacing the heart includes:

(a) measuring a local physiological value at a plurality of locations in the heart;
(b) determining a pacing regime which will change the distribution of the value at the plurality of locations; and
(c) pacing the heart using the new pacing regime.

Preferably, the new pacing regime is determined such that the stress on certain portions of the heart will be reduced, preferably, by keeping the local physiological value within a range. Further preferably, the range is locally determined based on local conditions in the heart. One preferred local physiological value is blood perfusion. Preferably, (a)–(c) are performed substantially in real time. Further preferably, measuring the physiological value is performed substantially simultaneously at the plurality of locations.

Still another aspect of the invention relates to increasing the efficiency of a heart using adaptive pacing. A preferred method of adaptive pacing includes:

(a) determining a preferred pacing regime for a heart which is optimal with respect to a physiological variable; and
(b) pacing the heart using the preferred pacing regime.

Preferably, the preferred pacing regime is determined using a map of the heart. The map is preferably analyzed to determine which portions of the heart are under-utilized due to their activation time. The preferred pacing is preferably initiated by implanting a pacer, preferably, with a plurality of electrodes. Alternatively or additionally, the preferred pacing is initiated by changing the electrification of a plurality of previously implanted pacemaker electrodes.

In a preferred embodiment of the invention, the pacing regime is regularly changed so that each pacing regime optimizes the utilization of different portions of the heart. Additionally or alternatively, the pacing regime is regularly changed to temporally distribute workload between different portions of the heart.

Another aspect of the invention relates to pacemakers having adaptive pacing regimes. A preferred pacemaker includes:

a plurality of electrodes;
a source of electricity for electrifying the electrodes; and
a controller which changes the electrification of the electrodes in response to a plurality of measured local physiological values of a heart to achieve an optimization of a physiological variable of the heart.

The measured physiological values preferably include plateau length and/or activation time. Preferably, the measurement is performed using the pacemaker electrodes. Alternatively or additionally, measurement is performed using at least one additional sensor. One preferred physiological variable is stroke volume. Further preferably, the physiological variable is measured by the pacemaker, such as measuring intra-cardiac pressure using a solid-state pressure sensor.

There is therefore provided in accordance with a preferred embodiment of the invention, a method of constructing a cardiac map of a heart having a heart cycle including:

(a) bringing an invasive probe into contact with a location on a wall of the heart;
(b) determining, at at least two different phases of the heart cycle, a position of the invasive probe;
(c) determining a local non-electrical physiological value at the location;
(d) repeating (a)–(c) for a plurality of locations of the heart; and (e) combining the positions to form a time-dependent map of at least a portion of the heart. Preferably, the method includes:

(f) determining at least one local relationship between changes in positions of the invasive probe and a determined local non-electrical physiological value.

There is provided in accordance with another preferred embodiment of the invention, a method of constructing a cardiac map of a heart having a heart cycle including:

(a) bringing an invasive probe into contact with a location on a wall of the heart;

(b) determining a position of the invasive probe;

(c) determining a local non-electrical physiological value at the location at a plurality of different phases of the heart cycle;

(d) repeating (a)–(c) for a plurality of locations of the heart; and (e) combining the positions to form a map of at least a portion of the heart. Preferably, the method includes determining at least a second position of the invasive probe at a phase at which the local non-electrical value is found, which position is different from the position determined in (b). Preferably, the method includes determining at least one local relationship between changes in positions of the invasive probe and determined local non-electrical physiological values.

Preferably, the method includes determining a trajectory of the probe as a function of the cardiac cycle. Preferably, the method includes analyzing the trajectory.

Additionally or alternatively, the local physiological value is determined using a sensor external to the probe. Preferably, the sensor is external to a body which includes the heart. Alternatively, the local physiological value is determined using a sensor in the invasive probe. Alternatively or additionally, the local physiological value is determined at substantially the same time as the position of the invasive probe. Alternatively or additionally, the map includes a plurality of maps, each of which corresponds to a different phase of the cycle of the heart. Alternatively or additionally, the map includes a difference map between two maps, each of which corresponds to a different phase of the cycle of the heart. Alternatively or additionally, the local physiological value includes a chemical concentration.

Alternatively or additionally, the local physiological value includes a thickness of the heart at the location. Preferably, the thickness of the heart is determined using an ultrasonic transducer mounted on the invasive probe. Preferably, the method includes determining a reaction of the heart to an activation signal by analyzing changes in the thickness of the heart.

Alternatively or additionally, the local physiological value includes a measure of a perfusion at the location. Alternatively or additionally, the local physiological value includes a measure of work performed at the location. Alternatively or additionally, the method includes determining a local electrical activity at each of the plurality of locations of the heart. Preferably, the electrical activity includes a local electrogram. Alternatively or additionally, the electrical activity includes a local activation time. Alternatively or additionally, the electrical activity includes a local plateau duration of heart tissue at the location. Alternatively or additionally, the electrical activity includes a peak-to-peak value of a local electrogram.

Alternatively or additionally, the method includes determining a local change in the geometry of the heart. Preferably, the local change includes a change in a size of an area surrounding the location. Alternatively or additionally, the local change includes a warp of an area surrounding the location. Alternatively or additionally, the local change includes a change in a local radius of the heart at the location. Preferably, the method includes determining an intracardiac pressure of the heart. Preferably, the method includes determining a relative tension at the location. Preferably, the relative tension is determined using Laplace's law.

In a preferred embodiment of the invention, the method includes determining an absolute tension at the location.

In a preferred embodiment of the invention, the method includes determining a movement of the location on the heart wall relative to the movement of neighboring locations. Alternatively or additionally, the method includes determining the activity of the heart at the location. Preferably, determining the activity includes determining a relative motion profile of the location on the heart wall relative to neighboring locations. Alternatively, the activity includes determining a motion profile of the heart at the location.

In a preferred embodiment of the invention, the method includes monitoring stability of the contact between the invasive probe and the heart. Preferably, monitoring includes monitoring the stability of the contact between the probe and the heart based on the motion profile. Alternatively or additionally, monitoring includes detecting changes in the motion profile for different heart cycles. Alternatively or additionally, monitoring includes detecting differences in positions of the probe at the same phase for different heart cycles. Alternatively or additionally, monitoring includes detecting changes in a locally measured impedance of the invasive probe to a ground. Alternatively or additionally, monitoring includes detecting artifacts in a locally determined electrogram.

In a preferred embodiment of the invention, the method includes reconstructing a surface of a portion of the heart. Alternatively or additionally, the method includes binning local information according to characteristics of the cycle of the heart. Preferably, the characteristics include a heart rate. Alternatively or additionally, the characteristics include a morphology of an ECG of the heart. Preferably, the ECG is a local electrogram. Alternatively or additionally, the method includes separately combining the information in each bin into a map. Preferably, the method includes determining differences between the maps.

In a preferred embodiment of the invention, the positions of the invasive probe are positions relative to a reference location. Preferably, the reference location is a predetermined portion of the heart. Alternatively or additionally, a position of the reference is determined using a position sensor. Alternatively or additionally, the method includes periodically determining a position of the reference location. Preferably, the position of the reference location is acquired at the same phase in different cardiac cycles.

In a preferred embodiment of the invention, the invasive probe is located in a coronary vein or artery. Alternatively, the invasive probe is located outside a blood vessel.

In a preferred embodiment of the invention, local information is averaged over a plurality of cycles.

There is also provided in accordance with a preferred embodiment of the invention, a method of determining the effect of a treatment including constructing a first map of a heart, prior to the treatment; constructing a second map of the heart, after the treatment; and comparing the first and second maps to diagnose the effect of the treatment.

There is also provided in accordance with a preferred embodiment of the invention, a method including constructing a map of a heart; and analyzing the map to determine underutilized portions of the heart.

There is also provided in accordance with a preferred embodiment of the invention, a method including constructing a map of a heart; and analyzing the map to select a procedure for treating the heart.

There is also provided in accordance with a preferred embodiment of the invention, a method including constructing a map of a heart; and analyzing the map to determine optimization possibilities in the heart.

There is also provided in accordance with a preferred embodiment of the invention, a method including constructing a map of a heart; and analyzing the map to determine underperfused portions of the heart.

There is also provided in accordance with a preferred embodiment of the invention, a method including constructing a map of a heart; and analyzing the map to determine overstressed portions of the heart.

There is also provided in accordance with a preferred embodiment of the invention, a method including constructing a map of a heart; and analyzing the map to determine local pathologies in the heart.

There is also provided in accordance with a preferred embodiment of the invention, a method including constructing a map of a heart; and analyzing the map to assess the viability of portions of the heart.

There is also provided in accordance with a preferred embodiment of the invention, a method of determining the effect of a change in activation of a heart, including constructing a first map of a heart, prior to the change; constructing a second map of the heart, after the change; and comparing the first and second maps to diagnose the effect of the change in activation.

There is also provided in accordance with a preferred embodiment of the invention, a method of determining the effect of a change in activation of a heart, including constructing a first map of a heart, prior to the change; constructing a second map of the heart, after the change; constructing a second map of the heart; and comparing the first and second maps, wherein the two maps are acquired in parallel by acquiring local information at a location over several cardiac cycles, wherein the activation changes during the several cardiac cycles.

There is also provided in accordance with a preferred embodiment of the invention, a method of assessing viability including constructing a first map of a heart, prior to a change in activation of the heart; constructing a second map of the heart, after the change; and comparing the first and second maps to assess the viability of portions of the heart. Preferably, changing the activation includes changing a pacing of the heart. Alternatively or additionally, changing the activation includes subjecting the heart to chemical stress. Alternatively or additionally, changing the activation includes subjecting the heart to physiological stress.

In a preferred embodiment of the invention, the heart is artificially paced.

There is also provided in accordance with a preferred embodiment of the invention, a method of cardiac shaping including generating a map of a heart; choosing a portion of the heart having a certain amount of muscle tissue thereat; and determining a pacing regime for changing the workload of the portion. Preferably, the method includes pacing the heart using the determined pacing regime. Preferably, the method includes waiting a period of time; then determining the effect of the pacing regime; and repeating choosing, determining and pacing if a desired effect is not reached.

Preferably, the workload of the portion is increased in order to increase the amount of muscle tissue therein. Alternatively, the workload of the portion is decreased in order to decrease the amount of muscle tissue thereat. In a preferred embodiment of the invention, the workload is changed by changing an activation time of the portion. Preferably, the map includes electrical activation information. Alternatively or additionally, the map includes mechanical activation information.

There is also provided in accordance with a preferred embodiment of the invention, a method of determining an optimal location for implanting a pacemaker electrode including:

(a) pacing a heart from a first location;

(b) determining a cardiac parameter associated with pacing at the location; and (c) repeating (a) and (b) for a second location; and (d) selecting an optimal location based on the determined values for the cardiac parameters. Preferably, the method includes:

(e) implanting the electrode at the location for which the cardiac parameter is optimal.

Preferably, pacing a heart includes bringing an invasive probe having an electrode to a first location and electrifying the electrode with a pacing current.

Preferably, the cardiac parameter includes stroke volume. Alternatively or additionally, the cardiac parameter includes intra-cardiac pressure. Alternatively or additionally, determining the cardiac parameter includes measuring the cardiac parameter using an invasive probe.

There is also provided in accordance with a preferred embodiment of the invention, a method of determining a regime for pacing a heart, including:

(a) determining a local physiological value at a plurality of locations in the heart; and (b) determining a pacing regime which changes a distribution of the physiological value in a desired manner. Preferably, the distribution includes a temporal distribution. Alternatively or additionally, the distribution includes a spatial distribution. Preferably, the method includes pacing the heart using the determined pacing regime. Alternatively or additionally, changing the distribution includes maintaining physiological values within a given range. Preferably, the range includes a locally determined range. Alternatively or additionally, the range includes a phase dependent range, whereby a different range is preferred for each phase of a cardiac cycle. Alternatively or additionally, the range includes an activation dependent range, whereby a different range is preferred for each activation profile of the heart. Preferably, different heart rates have different ranges. Alternatively or additionally, different arrhythmia states have different ranges.

In a preferred embodiment of the invention, the physiological values are determined substantially simultaneously. Preferably, the physiological value includes perfusion. Alternatively or additionally, the physiological value includes stress. Alternatively or additionally, the physiological value includes plateau duration.

There is also provided in accordance with a preferred embodiment of the invention, a method of determining a preferred pacing regime, including generating a map of the heart; and determining, using the map, a preferred pacing regime for a heart which is optimal with respect to a physiological variable. Preferably, the method includes pacing the heart using the preferred pacing regime. Alternatively or additionally, the map includes an electrical map.

Preferably, determining a preferred pacing regime includes generating a map of the activation profile of the heart. Alternatively or additionally, the map includes a mechanical map. Preferably, determining a preferred pacing regime includes generating a map of the reaction profile of the heart. Alternatively or additionally, the method includes analyzing an activation map or a reaction map of the heart to determine portions of the heart which are under-utilized due to an existing activation profile of the heart. Alternatively or additionally, pacing is initiated by implanting at least one pacemaker electrode in the heart. Preferably, the at least one pacemaker electrode includes a plurality of individual electrodes, each attached to a different portion of the heart.

In a preferred embodiment of the invention, pacing is initiated by changing the electrification of a plurality of previously implanted pacemaker electrodes. Alternatively or additionally, the physiological variable includes a stroke volume. Alternatively or additionally, the physiological variable includes a ventricular pressure profile.

There is also provided in accordance with a preferred embodiment of the invention, a method of pacing including:

(a) pacing a heart using a first pacing scheme; and (b) changing the pacing scheme to a second pacing scheme, wherein the change in pacing is not directly related to a sensed or predicted arrhythmia, fibrillation or cardiac output demand in the heart. Preferably, each of the pacing regimes optimizes the utilization of different portions of the heart. Alternatively or additionally, the changing of the pacing regimes temporally distributes workload between different portions of the heart.

There is also provided in accordance with a preferred embodiment of the invention, a pacemaker which performs any of the above described pacing based methods.

There is also provided in accordance with a preferred embodiment of the invention, a pacemaker including: a plurality of electrodes; a source of electricity for electrifying the electrodes; and a controller which changes the electrification of the electrodes in response to a plurality of values of local information of a heart, measured at different locations, to achieve an optimization of a cardiac parameter of the heart. Preferably, the local information is measured using the electrodes. Alternatively or additionally, the local information is measured using a sensor.

There is also provided in accordance with a preferred embodiment of the invention, a pacemaker including: a plurality of electrodes; a source of electricity for electrifying the electrodes; and a controller which changes the electrification of the electrodes in response to a stored map of values of local information of a heart at different locations, to achieve an optimization of a cardiac parameter of the heart.

Preferably, the local information includes a local activation time. Alternatively or additionally, the local information includes a local plateau duration. Alternatively or additionally, the local information includes local physiological values. Alternatively or additionally, the local information includes phase dependent local positions. Alternatively or additionally, the cardiac parameter includes a stroke volume. Alternatively or additionally, the cardiac parameter is measured by the pacemaker. Alternatively or additionally, the cardiac parameter includes an intracardiac pressure.

There is also provided in accordance with a preferred embodiment of the invention, a method of detecting structural anomalies in a heart, including:

(a) bringing an invasive probe into contact with a location on a wall of the heart;

(b) determining a position of the invasive probe;

(c) repeating (a)–(b) for a plurality of locations on the wall;

(d) combining the positions to form a time-dependent map of at least a portion of the heart; and (e) analyzing the map to determine structural anomalies in the heart. Preferably, the structural anomaly is an insipid aneurysm.

Preferably, the method includes repeating (b) at least a second time, at the same location and at a different phase of the cardiac cycle than (b).

There is also provided in accordance with a preferred embodiment of the invention, a method of adding a conductive pathway in a heart between a first segment of the heart and a second segment of the heart, including: generating a mechanical map of the heart; providing an activation conduction device having a distal end and a proximal end; electrically connecting the distal end of the device to the first segment; and electrically connecting the proximal end of the device to the second segment.

There is also provided in accordance with a preferred embodiment of the invention, a conductive device for creating conductive pathways in the heart, including: a first lead adapted for electrical connection to a first portion of the heart; a second lead adapted for electrical connection to a second portion of the heart; a capacitor for storing electrical charge generated at the first portion of the heart and for discharging the electrical charge at the second portion of the heart.

There is also provided in accordance with a preferred embodiment of the invention, a method of viewing a map, including: providing a map of local information of a heart; and overlaying a medical image on the map. Preferably, the medical image is an angiogram. Alternatively or additionally, the medical image is a three-dimensional image. Alternatively or additionally, the map contains both spatial and temporal information.

There is also provided in accordance with a preferred embodiment of the invention, a method of diagnosis including: generating a map of a heart; and correlating the map with a library of maps. Preferably, the method includes diagnosing the condition of the heart based on the correlation.

There is also provided in accordance with a preferred embodiment of the invention, apparatus including: a memory having a plurality of maps stored therein; and a correlator which correlates an input map with the plurality of maps.

There is also provided in accordance with a preferred embodiment of the invention, a method of analysis, including generating a map of electrical activation of a heart; generating a map of mechanical activation of the heart; and determining local relationships between the local electrical activation and mechanical activation. Preferably, the mechanical activation includes a profile of movement. Preferably, the electrical activation includes an activation time.

There is also provided in accordance with a preferred embodiment of the invention, apparatus adapted to generate a map in accordance with any of the mapping methods described herein. Preferably, the apparatus includes a display adapted to display the map.

Although the description of the present invention focuses on the heart, apparatus and methods described herein are also useful for mapping and affecting other organs, such as the stomach and other muscles. For example, in treating atrophied muscles using stimulation, an electromechanical map of the muscle is preferably acquired during a test stimulation to help in determining and optimal stimulation regime.

BRIEF DESCRIPTION OF THE DRAWINGS

FIGS. 5A–C are partial schematic cross-sectional perspective views of a heart showing application of Laplace's law to the determination of tension in the heart muscle;

DETAILED DESCRIPTION OF THE PREFERRED EMBODIMENTS

Figure 1A:
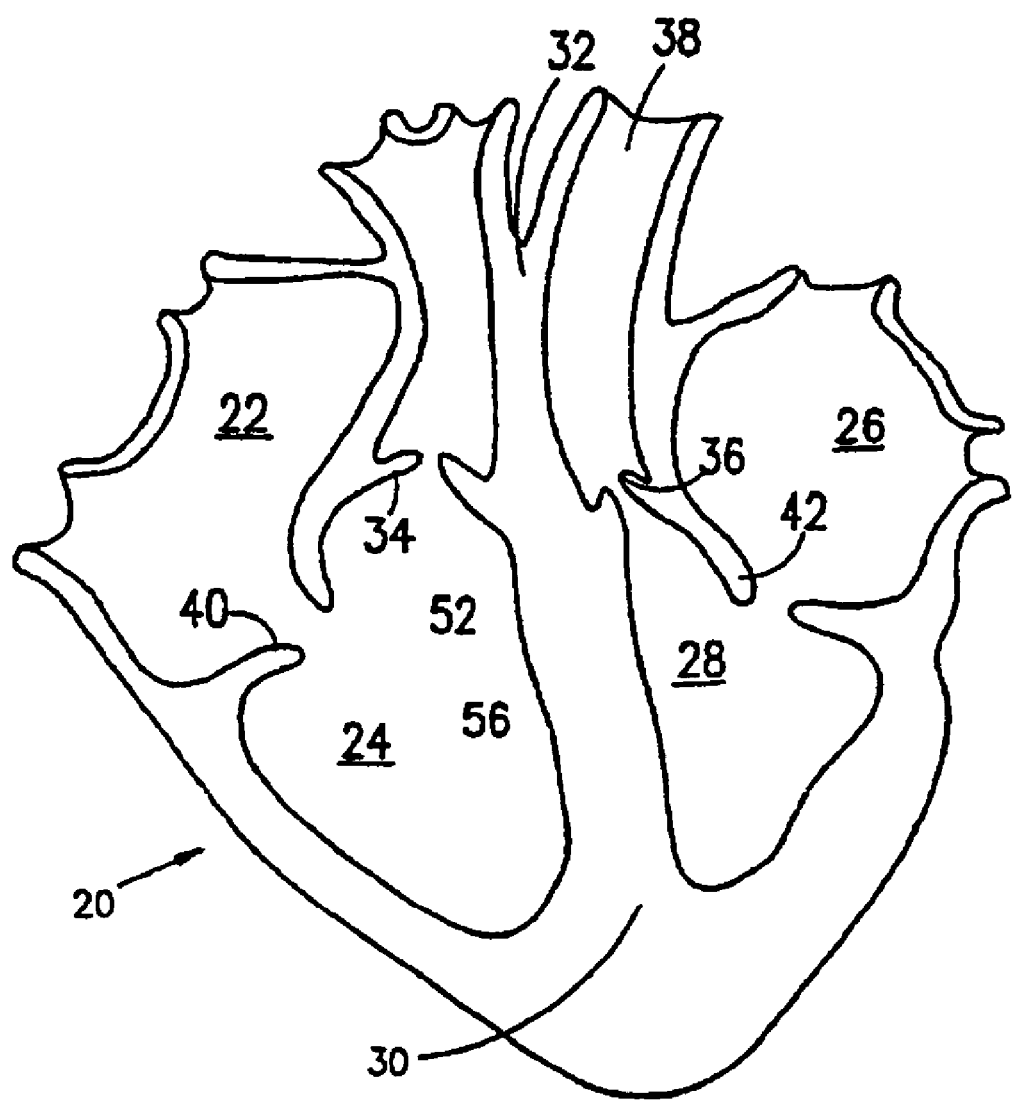
FIG. 1A is a schematic cross-section diagram of a heart.
Figure 1B:
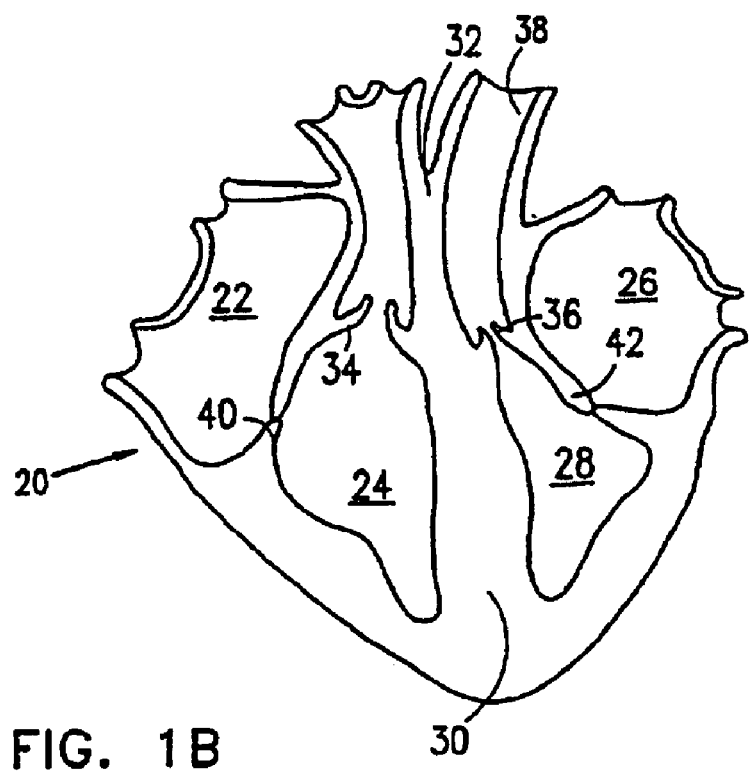
FIGS. 1B–1E are schematic cross-section diagrams showing the heart in each of four phases of a cardiac cycle.
Figure 1C:
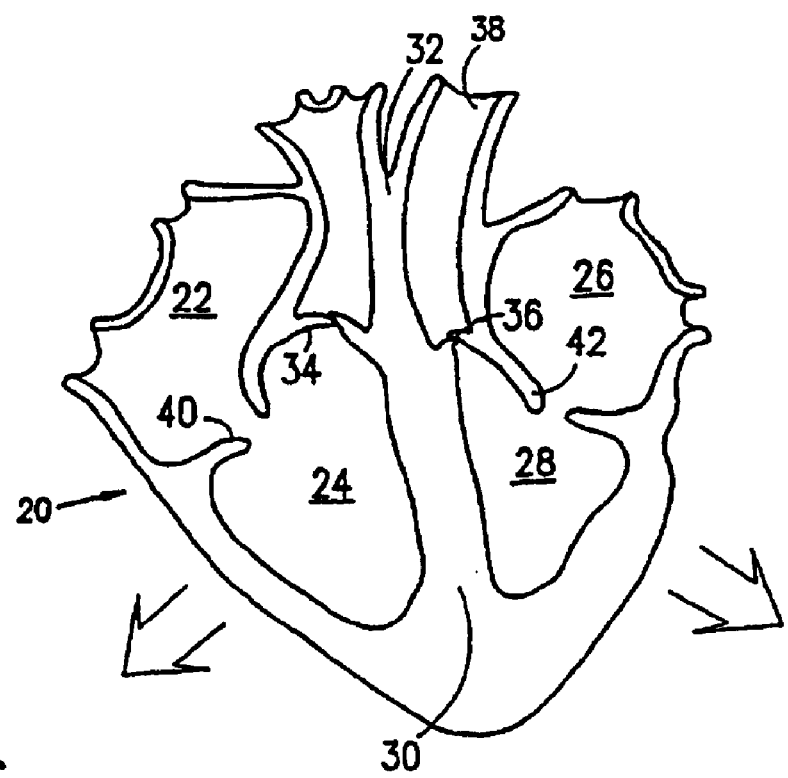
Figure 1D:
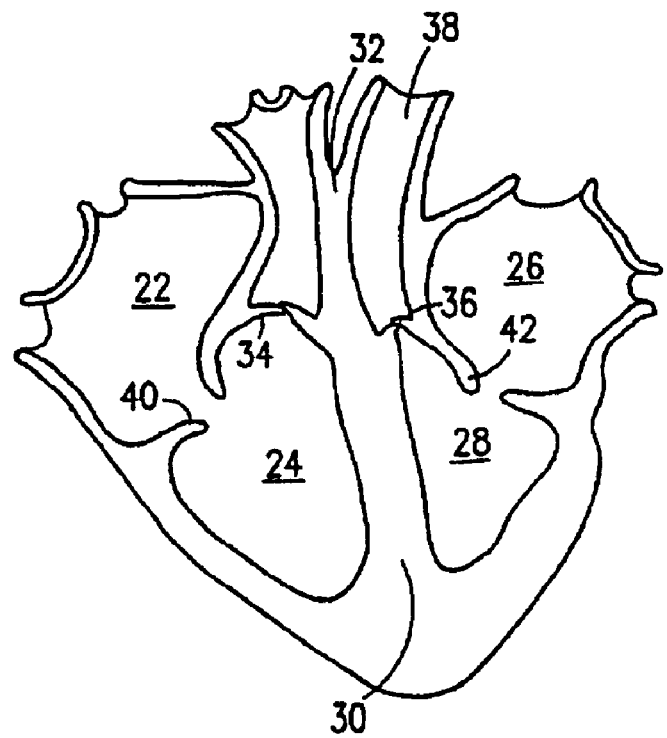
Figure 1E:
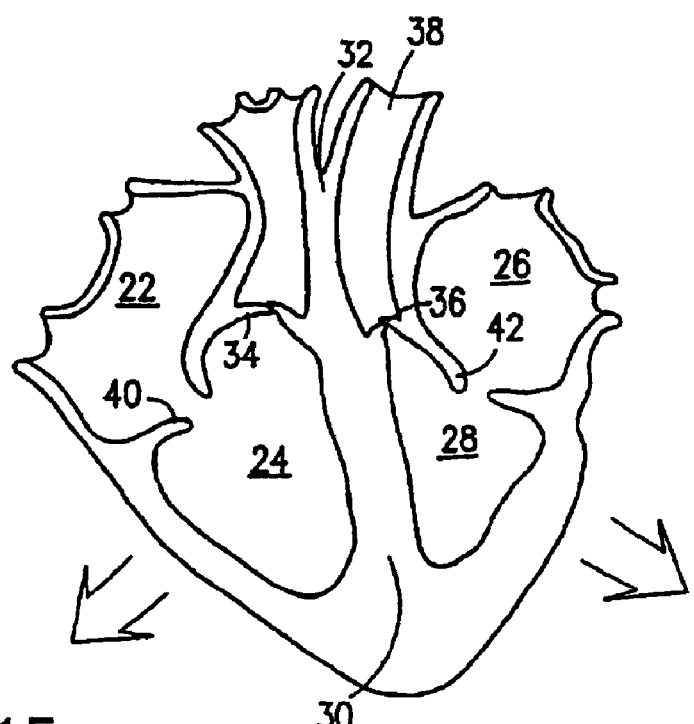
Figure 1F:
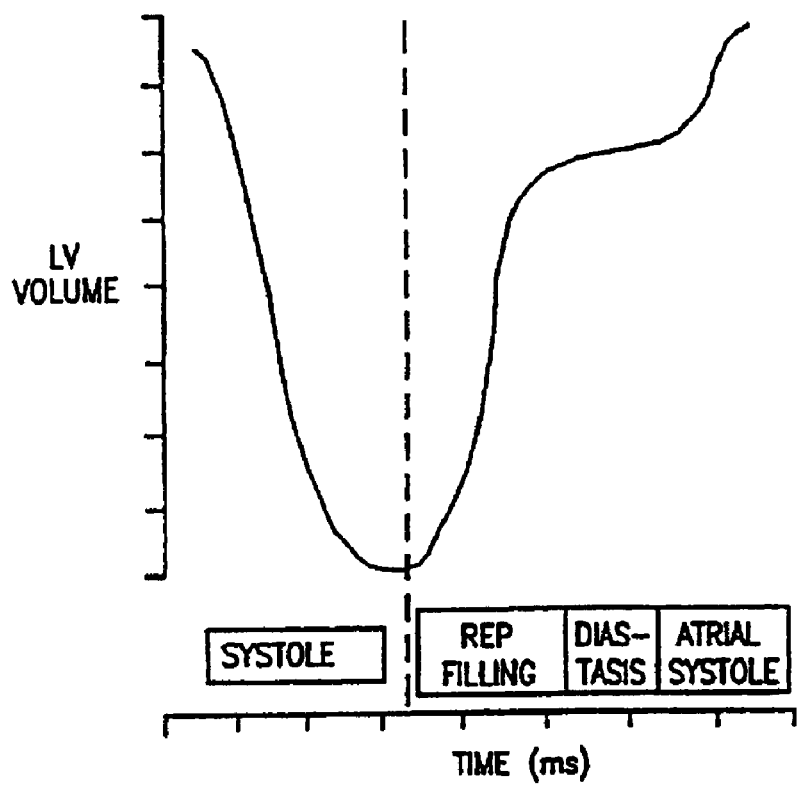
FIG. 1F is a graph showing the blood volume in a left ventricle of the heart during a cardiac cycle.
Figure 1G:
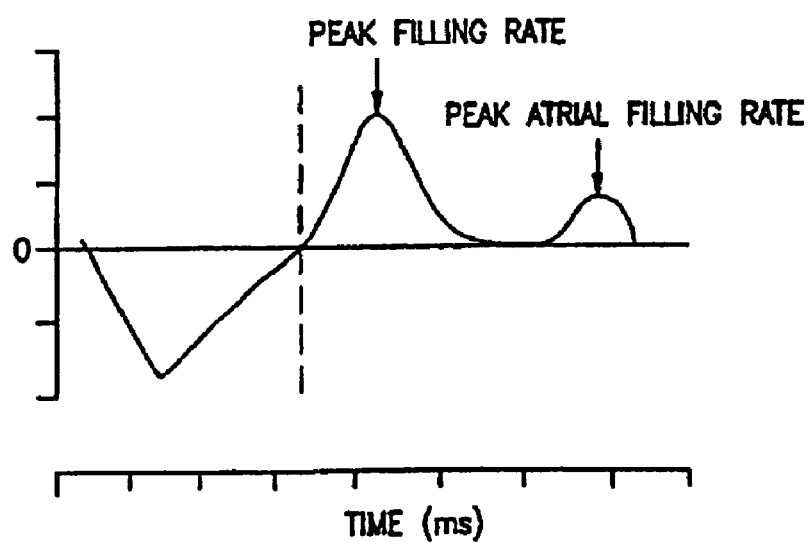
FIG. 1G is a graph showing the filling rate of the left ventricle during a cardiac cycle.
Figure 2:
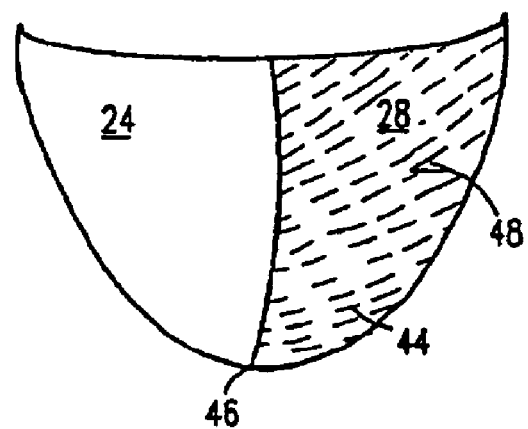
FIG. 2 is a partial schematic view of a heart showing the arrangement of cardiac muscle fibers around a left ventricle.
Figure 3:
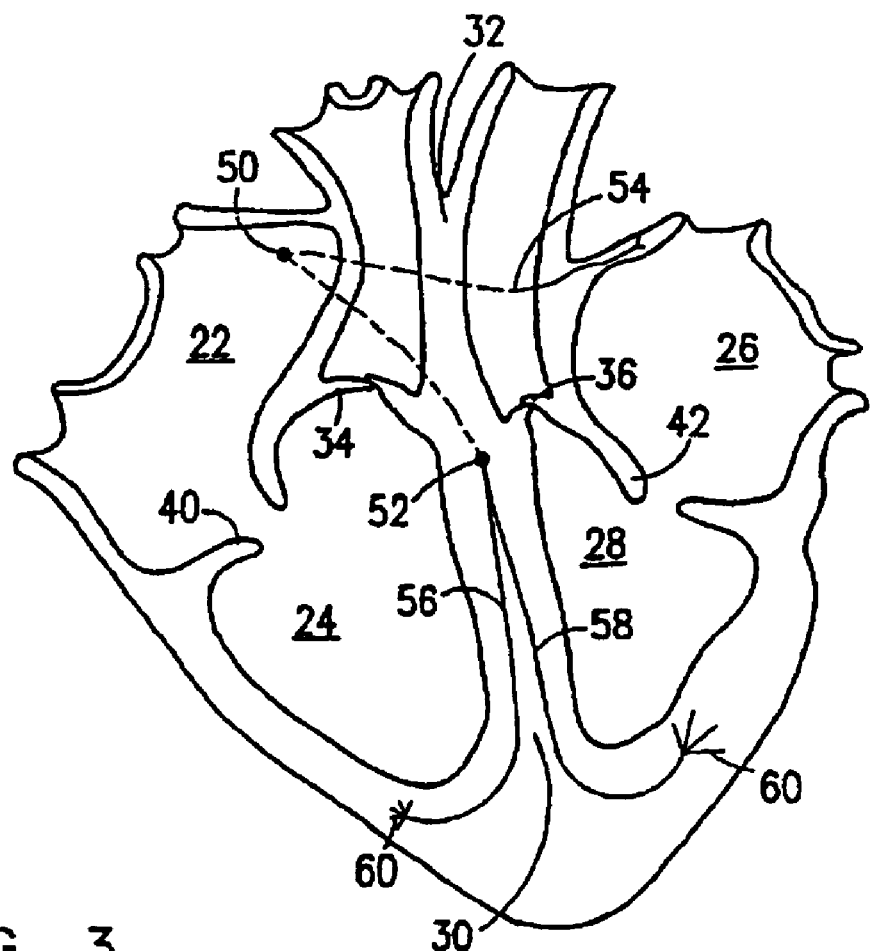
FIG. 3 is a schematic cross-section diagram of a heart showing the electrical conduction system of the heart.
Figure 4:
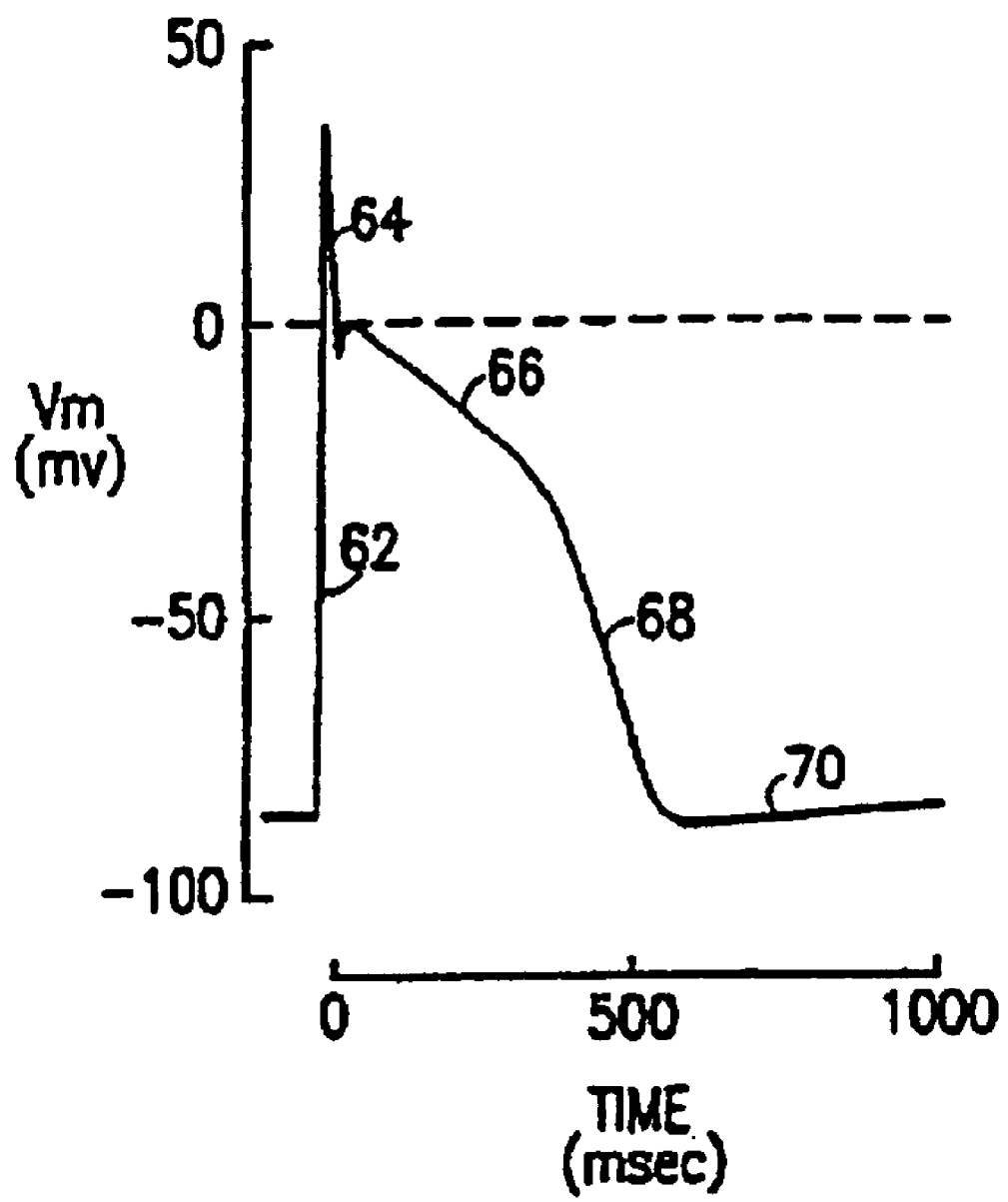
FIG. 4 is a graph showing changes in the voltage potential of a single cardiac muscle cell in reaction to an activation signal.
Figure 6:
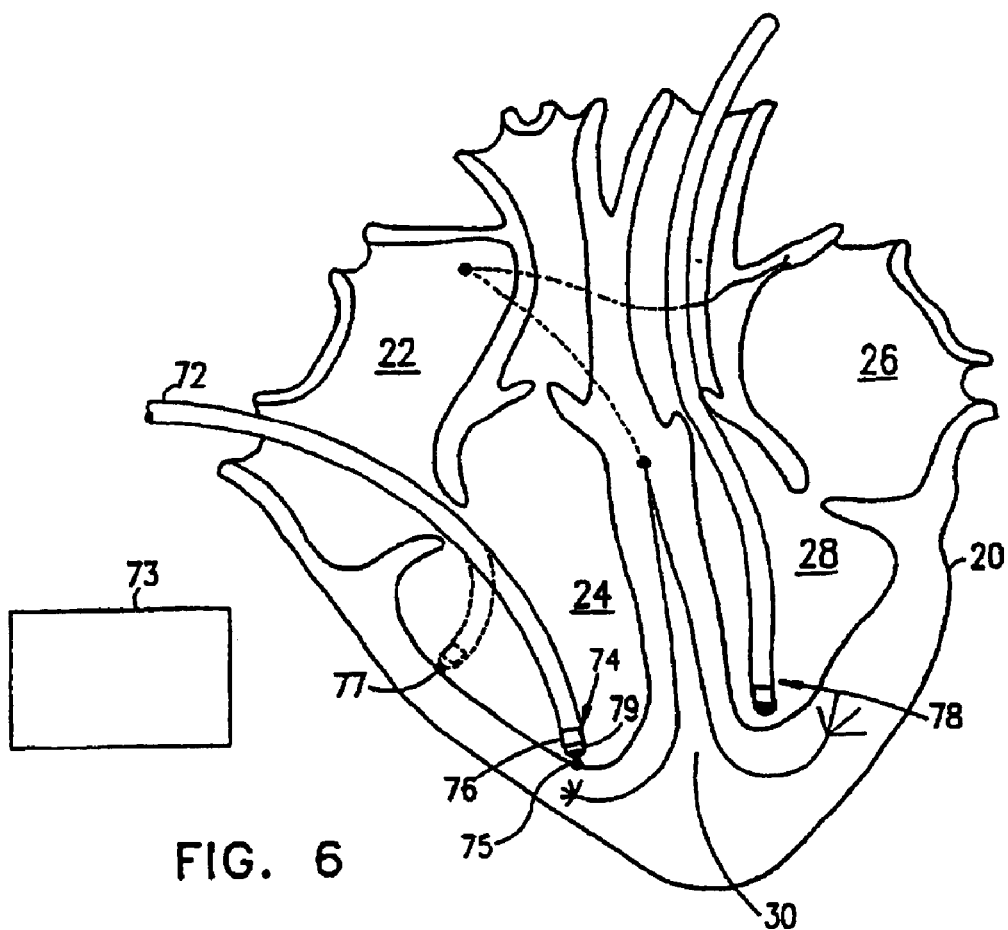
FIG. 6 is a schematic cross-sectional side view of a heart showing a preferred apparatus for generating a map of the heart.
Figure 7:
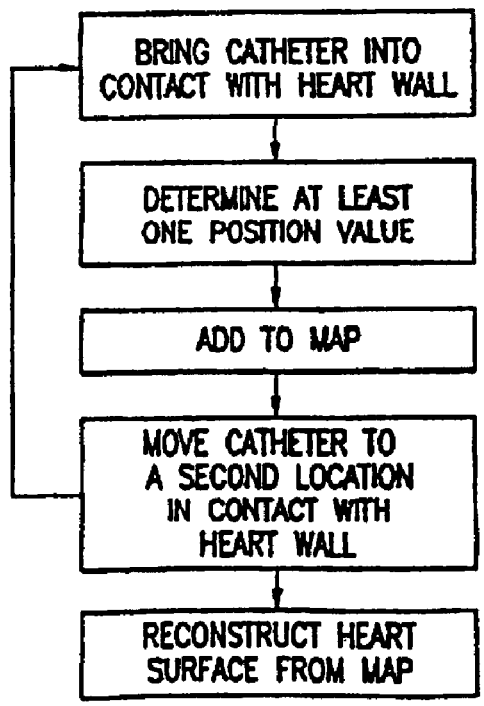
FIG. 7 is a flowchart of a preferred method of constructing the map utilizing the apparatus of FIG. 6.

A first preferred embodiment of the invention relates to mapping the geometry of the heart and time related changes in the geometry of the heart. FIG. 6 is a schematic side view of a preferred apparatus for performing the mapping. FIG. 7 is a flowchart showing a preferred method for performing a mapping.

Referring to FIG. 6, a distal tip 74 of a mapping catheter 72 is inserted into heart 20 and brought into contact with heart 20 at a location 75. Preferably, the position of tip 74 is determined using a position sensor 76. Sensor 76 is preferably a position sensor as described in PCT application US95/01103, "Medical diagnosis, treatment and imaging systems", filed Jan. 24, 1995, in U.S. Pat. No. 5,391,199 or in U.S. Pat. No. 5,443,489, all assigned to the same assignee as the instant application and the disclosures of which are incorporated herein by reference, and which typically require an external magnetic field generator 73. Alternatively, other position sensors as known in the art are used, for example, ultrasonic, RF and rotating magnetic field sensors. Alternatively or additionally, tip 74 is marked with a marker whose position can be determined from outside of heart 20, for example, a radio-opaque marker for use with a fluoroscope. Preferably, at least one reference catheter 78 is inserted into heart 20 and placed in a fixed position relative to heart 20. By comparing the positions of catheter 72 and catheter 78, the position of tip 74 relative to the heart can be accurately determined even if heart 20 exhibits overall motion within the chest. Preferably the positions are compared at least once every cardiac cycle, more preferably, during diastole. Alternatively, position sensor 76 determines the position of tip 74 relative to catheter 78, for example, using ultrasound, so no external sensor or generator 73 is required. Alternatively, catheter 78 is outside the heart, such as outside the body or in the esophagus.

It should be appreciated that a geometric map can be constructed even if position sensor 76 only determines position and not orientation. However, since sensor 76 is typically located at a small distance from tip 74, at least two orientation angles are desirable to increase the accuracy of the position determination of tip 74.

Referring to FIG. 7, a typical mapping process includes:
(a) bringing catheter tip 74 into contact with the wall of heart 20, at location 75;
(b) determining at least one position of tip 74;
(c) adding the position value to the map;
(d) moving catheter 72 to a second location, such as a location 77;
(e) repeating steps (b)–(d); and
(f) (optionally) reconstructing the surface of heart 20 from the determined positions.

Reconstructing the surface of heart 20 may comprise reconstructing inner or outer surfaces of heart 20, depending on the location of catheter tip 74. Methods of reconstructing a surface from a plurality of data points are well known in the art.

Preferably, catheter 72 is a steerable tip catheter, so that repositioning of tip 74 is facilitated. Steerable catheters are further described in PCT application US95/01103 and in U.S. Pat. Nos. 5,404,297, 5,368,592, 5,431,168, 5,383,923, 5,368,564, 4,921,482, 5,195,968, the disclosures of which are incorporated herein by reference.

In a preferred embodiment of the invention, each position value has an associated time value, preferably relative to a predetermined point in the cardiac cycle. Preferably, multiple position determinations are performed, at different points in the cardiac cycle, for each placement of tip 74. Thus, a geometric map comprises a plurality of geometric snapshots of heart 20, each snapshot associated with a different instant of the cardiac cycle. The cardiac cycle is preferably determined using a standard ECG device. Alternatively or additionally, a local reference activation time is determined using an electrode on catheter 72. Heart 20 may be paced in a known manner, such as by catheter 78 or may be naturally paced.

In an alternative preferred embodiment of the invention, position values are acquired also while tip 74 is not in contact with heart 20. These position values can be used to help generation of an image of the inner surface of heart 20 by a process of elimination, since any point inside the heart, not in contact with the surface, is not on its inner surface.

As can be appreciated, contact between tip 74 and heart 20 must be assured. In particular, it is important to know when tip 74 comes into contact with heart 20 after repositioning of tip 74 and the stability of tip 74 at a location, such as whether tip 74 moves from location 75 without operator intervention as a result of motion of heart 20 must be known. One method of monitoring the contact between tip 74 and location 75 is through analysis of the trajectory of tip 74. The inner wall of heart 20 has many crevices and tip 74 typically lodges in one of these crevices, such that tip 74 moving together with location 75. It can be expected that tip 74 will return to the same spatial position each cardiac cycle. Thus, if tip 74 does not return to the same position each diastole, contact between tip 74 and location 75 is not stable. Further, some types of slippage can be detected by determining whether the entire trajectory of tip 74 substantially repeats itself Furthermore, some types of slippage add artifacts to the trajectory which can be detected by comparing the trajectory against trajectories of nearby segments of the heart or against a model of the motion of the heart.

It is also known that initiation of contact between tip 74 and heart 20 causes artifacts in a locally measured electrogram. Thus, in a preferred embodiment of the invention, tip 74 includes an electrode 79 which measures the local electrical activity. Artifacts in the measured activity indicate that tip 74 is not in stable contact with location 75. Preferably, the local electrical activity and in particular, the local activation time and local plateau length, are stored in association with each location in heart 20.

In an additional embodiment of the invention, the contact pressure between tip 74 and location 75 is measured, using a pressure sensor, to determine the existence and stability of contact therebetween.

In a preferred embodiment of the invention electrode 79 is used to measure the impedance between tip 74 and a ground outside the patient. The impedance between tip 74 and the ground is affected by the distance of tip 74 from the wall of heart and by the quality of contact therebetween. The effect can be explained in the following manner. Long cells such as muscle cells and nerves exhibit electrical conductivities which are non-isotropic and frequency dependent. Blood, which fills heart 20, exhibits conduction which is relatively frequency independent and isotropic, and its resistance is approximately half the average resistance of muscle tissue. The greatest amount of frequency dependence of body structures is found between 30 and 200 Hz. However, frequencies in the range 30 Hz–10 MHz are useful. For example, at 50 KHz, contact can be most easily determined from changes in the impedance and at 0.5 MHz, accumulation of residue on the catheter from charring of heart muscle during ablation can be determined from changes in the impedance.

Figure 8:
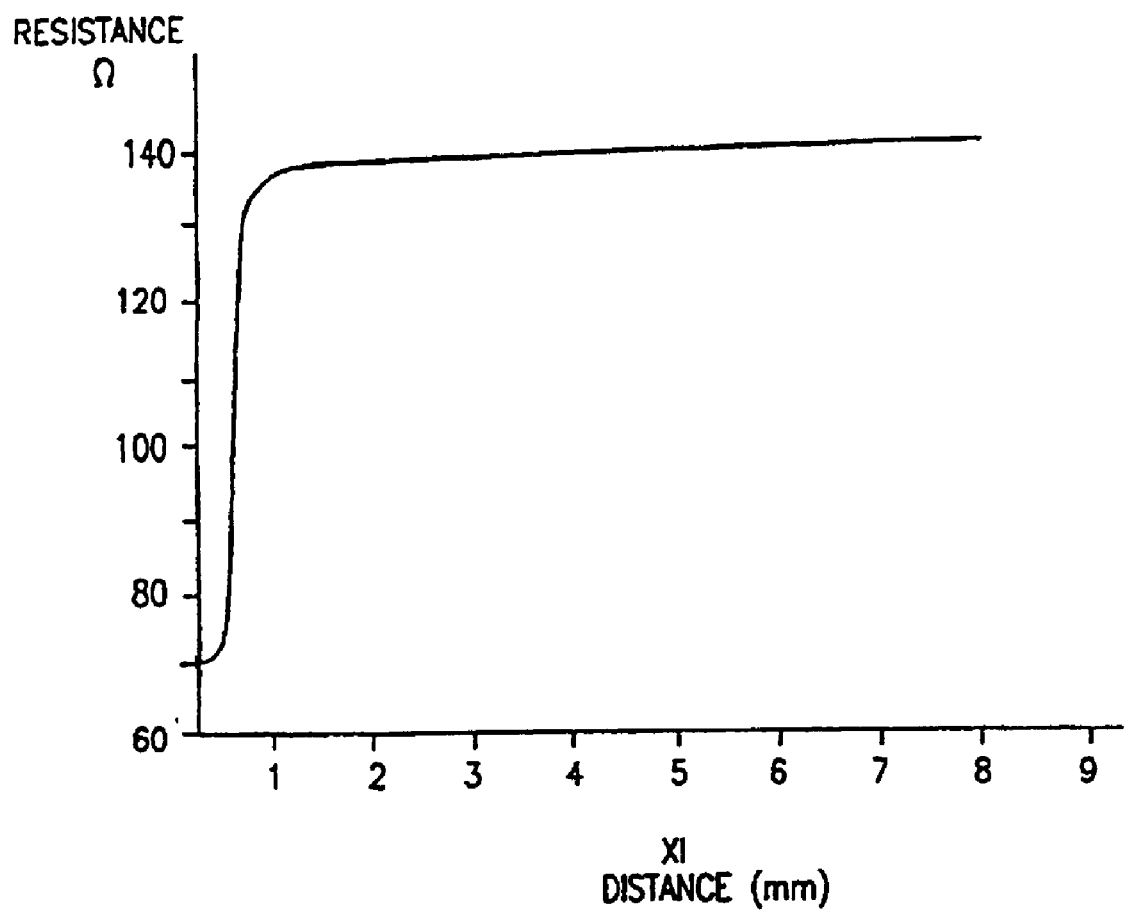
FIG. 8 is a generalized graph showing the dependence of a resistance on the distance of the catheter from heart muscle tissue.

FIG. 8 is a generalized graph showing the dependence of a resistance, between tip 74 and an external lead attached to the patient, on the distance of tip 74 from location 75, at 50 KHz.

Figure 9A:
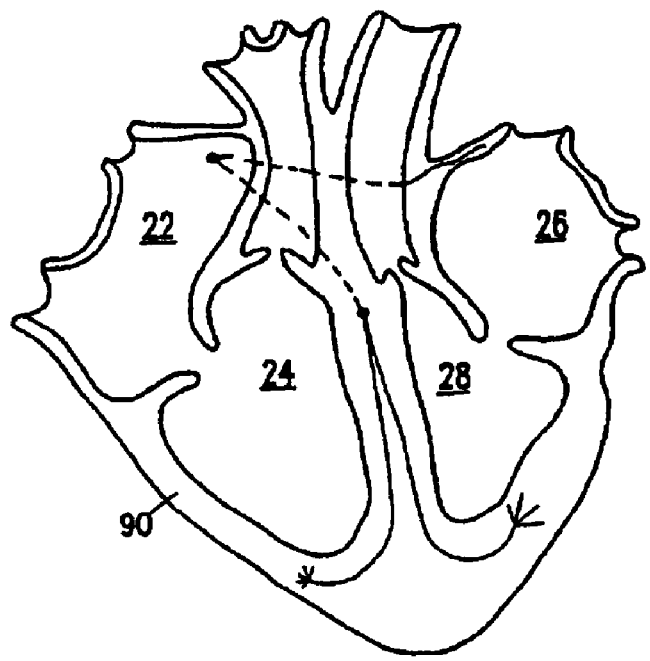
FIGS. 9A–D show various local changes in the geometry of the heart.
Figure 9B:
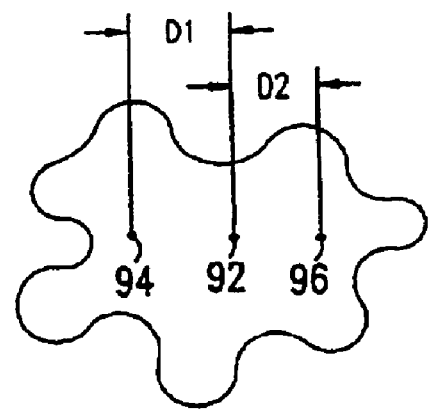
Figure 9C:
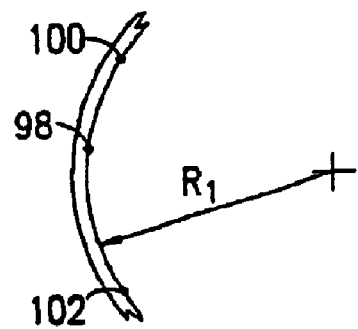
Figure 9D:
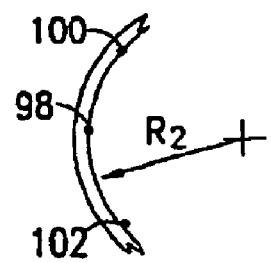

Local geometric changes in the heart are also clinically interesting. FIG. 9A shows a segment 90 of heart 20 and FIGS. 9B–9D show various aspects of local movement of segment 90. The timing of movement of segment 90 relative to the cardiac cycle and/or relative to the movement of other segments of heart 20 indicates forces acting at segment 90. These forces may be as a result of local contraction at segment 90 or as a result of contraction of other portions of heart 20. Movement of segment 90 before an activation signal reaches segment 90 may indicate that segment 90 is not activated at an optimal time and, thus, that it does not contribute a maximum amount to the output of heart 20. Movement without an activation signal usually indicates non-muscular tissue, such as scar tissue. The activation time is preferably measured using electrode 79 (FIG. 6).

FIG. 9B shows another way of determining the reaction of muscle tissue to an activation signal. A first location 92 is located a distance D1 from a second location 94 and a distance D2 from a third location 96. In a normal heart D1 and D2 can be expected to contract at substantially the same time by a substantially equal amount. However, if the tissue between location 92 and location 94 is non-reactive, D1 might even grow when D2 contracts (Laplace's law). In addition a time lag between the contraction of D1 and of D2 is probably due to blocks in the conduction of the activation signal. A map of the reaction of the heart to an activation signal may be as important as an activation map, since it is the reaction which directly affects the cardiac output, not the activation.

FIGS. 9C and 9D show the determination of local changes in the radius of heart 20, which can be together with the pressure to determine the local tension using Laplace's law. In FIG. 9C a plurality of locations 98, 100 and 102 exhibit a local radius R1 and in FIG. 9D, the local radius decreases to R2, which indicates that the muscle fiber at locations 98, 100 and 102 is viable. It should be noted, that since the pressure in heart 20 is spatially equalized, a ratio between the tension at different parts of heart 20 can be determined even if an absolute value cannot be determined.

Figure 10:
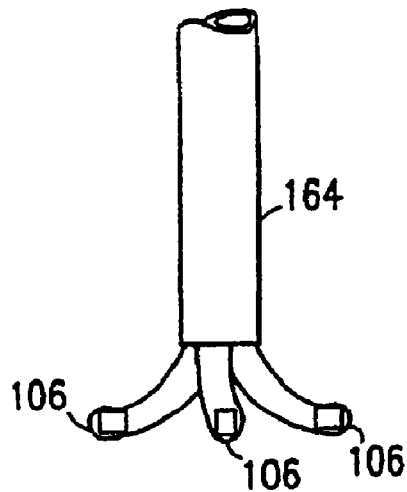
FIG. 10 shows a multi-headed catheter for sensing local geometric changes according to a preferred embodiment of the invention.

In a preferred embodiment of the invention, a plurality of catheters are placed at locations 98, 100 and 102, so that changes in the local geometry can be determined in a single cardiac cycle. Alternatively or additionally, a multi-head catheter, each head having a position sensor, is used to map local geometrical changes. FIG. 10 shows a multi-head catheter 104 having a plurality of position sensors 106 for mapping local geometric changes.

Another clinically important local change is a change in the thickness of a wall segment of heart 20. Muscle fibers thicken when they contract, so an increase in the thickness of the wall segment indicates that muscle fibers in the wall segment are contracting. Thinning of the wall segment indicates that the wall segment is stretching. Either there are not enough muscle fibers in the wall segment to overcome the tension on the wall segment or the muscle fibers in the wall segment are not activated in synchrony with the rest of heart 20, resulting in pressure increases which are not counteracted by local tension increases. Late increases in the thickness of the wall segment usually indicate that the activation signal was delayed at the segment. Local changes in thickness can also be compared to a locally determined activation time, to determine a local reaction time. In addition, comparison of differences in thickening between several adjacent wall segments is indicative of the activation time, much like changes in local geometry.

The local thickness of the wall segment is preferably determined using an ultrasonic sensor mounted on catheter 72 or catheter 78. Forward looking ultrasonic sensors (FLUS), suitable for mounting on catheter 72 for determining the local thickness of the wall segment are described in PCT application US95/01103 and in U.S. Pat. No. 5,373,849, the disclosures of which are incorporated therein by reference. A side looking ultrasonic sensor (SLUS), suitable for mounting on catheter 78 is described in PCT publication WO 95/07657, the disclosure of which is incorporated herein by reference. Alternatively or additionally, an external sensor, such as an echocardiograph determines the thickness of the wall segment adjacent tip 94.

In a preferred embodiment of the invention sensors, additional to position sensor 76, are mounted at tip 74. As already described, at least one electrode 79 is preferably mounted at tip 74 to map the local electrical activity which can be integrated with the geometric map to form an electromechanical map. For example, contraction duration can be compared to local electrical plateau length or local activation time can be compared to local reaction time using an electromechanical map.

Additionally or alternatively, a chemical sensor is mounted at tip 74 to determine changes in the local ionic concentrations or local chemical concentrations. Typically, such a chemical sensor is mounted on a needle which is inserted into the myocardium.

Alternatively or additionally, a perfusion meter is mounted on tip 74 to determine the amount of perfusion. Examples of perfusion meters include: a Doppler ultrasound perfusion meter or a Doppler laser perfusion meter, such as disclosed in "Design for an ultrasound-based instrument for measurement of tissue blood flow", by Burns, S. M. and Reid, M. H., in *Biomaterials. Artificial Cells and Artificial Organs*, Volume 17, Issue 1 page 61–68, 1989, the disclosure of which is incorporated herein by reference. Such a perfusion meter preferably indicates the flow volume and/or the flow velocity.

Alternatively or additionally, a scintillation detector is mounted on tip 74 to detect radiation emitted by radio-pharmaceuticals injected into or ingested by the patient. If a suitable low energy radio-pharmaceutical is used, the scintillation detector will be sensitive to radiation from portions of heart 20 substantially in contact with tip 74. For example, local perfusion can be determined.

In another preferred embodiment of the invention, an optical sensor is mounted on tip 74. As is known in the art, oxygenated blood reflects a spectrum which is different from the spectrum reflected by non-oxygenated blood. By determining the reflectance of portions of heart 20, the perfusion thereof can be determined. Additionally or alternatively, optical reflectivity patterns or texture is used to differentiate between different tissue types, for example, fibrous, viable muscle and damaged muscle. Preferably, the optical sensor is a camera or a fiber-optic image guide. Further preferably, an IR (infra-red) sensitive sensor is used. Typically, illumination at tip 74 is provided by a light source mounted on tip 74 or by light transmitted through a fiber-optic light-guide.

Alternatively or additionally, a cold-tip catheter is used to map the effect of ablating a portion of the heart. It is known in the art that hypothermic cardiac muscle does not initiate or react to electrical signals. Cold-tip catheters, such as disclosed in PCT publication WO 95/19738 of Jul. 25, 1995, the disclosure of which is incorporated herein by reference, can be used to inhibit the electrical activity of a local wall segment while simultaneously mapping the local geometrical effects of the inhibition.

Other locally sensed variables include, temperature, which may indicate perfusion or activation, osmolarity, conduction velocity, repolarization time, repolarization duration, and impedance, which may indicate tissue type and viability.

Mapping is typically performed when heart 20 is externally paced, such as using another catheter, either to set a constant heart rate or to generate certain arrhythmias. Electrode 79 is useful in identifying and analyzing arrhythmias. In addition electrode 79 can be used as a pacemaker to determine the effect of pacing from a certain location, such as initiating VT. The location of the catheter may be displayed as a relatively fixed location, such as end diastolic position. Alternatively, the movement of the catheter with the cardiac cycle is shown (with or without a changing map of the heart) as a navigational aid.

Several types of maps are generally acquired. One type maps local physiological values as a function of location on the heart, for example conductance. In this type of map, the position of tip 74 is typically determined at the same phase of the cardiac cycle for each new location and is unrelated to the acquisition of the local value. The local value may be time dependent. For example, a map of the instant local thickness of the heart wall as a function of the phase of the cardiac cycle. Another example is a local electrogram as a function of time. The value may be continuously acquired over the entire cardiac cycle, only over a portion thereof or at a single instant synchronized to the position determination and/or the cardiac cycle. A geometric map includes information about the geometry of the heart, for example shape and volume, and/or changes in the geometry of the heart as a function of time, for example, thickness, local curvature and shape. An electro-mechanical map includes information about the coupling between electrical signals and mechanical changes in the heart, for example, thickening as a function of activation time. Other types of maps include chemical-mechanical maps, which correlate mechanical and chemical action of the heart, energy expenditure maps which show local expenditures of energy, perfusion maps which show local perfusion of cardiac muscle and a map of the ratio between energy expenditure and local perfusion. One important type of map displays the delay between electrical activation time and various parameters of mechanical reaction. The mechanical reaction displayed may be a start of contraction, a maximum contraction or an end of contraction. Further, such a map may show the relative delays between any portion of the local electrical activity and the mechanical activity, for example, the electrical activity may be the end of the plateau or the beginning of the rapid depolarization. This information is useful in differentiated between healthy and diseased tissue, as the lag between electrical and mechanical activity tends to be more pronounced in diseased tissue.

Several different types of analysis are useful in preferred embodiments of the invention. In one, basic type of analysis, acquisition of local information is repeated at the same point over a number of cycles for binning. Preferably, the pacing of the heart is changed between the acquisitions and each measured value is associated with a particular pacing regime. Alternatively, this type of analysis may be practiced while performing ablations in the heart or otherwise changing the activation profile of the heart. Alternatively, the acquired values are averaged over several cardiac cycles to reduce noise.

In accordance with another preferred embodiment of the invention, the trajectory of the catheter is analyzed over a period of several cardiac cycles. This analysis is useful to determine changes in the activation profile of the heart over time or as a function of respiration and body position.

In a preferred embodiment of the invention, one or more different types of local analysis may be performed to assess cardiac function, locally and as a whole. One type of local analysis determines the location, velocity and or acceleration of the probe as a function of the cardiac cycle. Also, local voltage or any other type of local information may be used instead of position information. Such local information is expected to form a loop of values, where the values rises and/or lowers as a function of the cardiac cycle and returns to substantially the same value at the same phase of every cycle. In some diseased tissue, the loop may close (i.e., return to the same value at the same phase) only after several cycles. The stability of these loops is another indicator of cardiac health. The form of the loop may be compared between different locations to assess the relationship between the local information values and electrical activation time, mechanical activation and other indicators of the action potential, including the plateau start and end.

In accordance with a preferred embodiment of the invention, local mechanical activation and/or other local mechanical activity, such as the end of the contraction, may be determined based on a change in the velocity direction or in the acceleration direction at a location. It should be appreciated that the velocity and acceleration may be referred to as three dimensional vectors in space or as simple one dimensional vectors. Thus, one map in accordance with a preferred embodiment of the invention, graphs changes in the velocity and acceleration profile as a function of the movement of the catheter.

Another type of map in accordance with a preferred embodiment of the invention, shows the absolute peak-to-peak voltage at each location. In healthy tissue the value of this voltage may be one or more orders of magnitude higher than in scar tissue, with diseased tissue having intermediate values. Thus, different types of cardiac tissues may be identified based on the measured peak-to-peak voltage.

Another type of analysis relates to changes in area at a location. In a preferred embodiment of the invention, the surface of the heart is reconstructed using a star based algorithm, as polygons, preferably triangles, with each point being a location. The area surrounding a location is defined as the area in the polygons which include the location. One type of map in accordance with a preferred embodiment of the present invention shows the changes in the area surrounding the location as a function of time. The area generally indicates local contractile performance. Another type of analysis is determining warping of the polygons as a function of the cardiac cycle. This analysis can be used to calculate stress and/or strain at the location.

In a preferred embodiment of the invention, maps are compared before and after a medical procedure to assess its success. In addition, it may be desirable to compare maps taken at different times and at different levels of cardiac activity and demand, for example, before, during and after exercise. In some patients it may not be practical to perform exercise, so a chemical, test, such as using Dobutamine, may be applied instead of a physical stress test.

As explained above, maps can be used to determine clinical information about the heart. Preferably, maps are constructed and analyzed in preparation for a therapeutic procedure or in assessing the success of a therapeutic procedure. For example, scar tissue neither reacts to nor conducts an electrical signal, while hibernating muscle tissue conducts the activation signal but does not react to it. A map, as described above, can be used to differentiate between these and other types of tissue.

Aneurysms are readily detectable on a geometric map, as bulges during systole. Furthermore, potential aneurysms can be detected soon after an AMI (acute myocardial infraction) from local reactions to an activation signal and local reactions to changes in intracardiac pressure, even if they are not visible to the naked eye. Automatic detection may be based on paradoxical movement, in which an over-stressed portion of the heart expands (and bulges out) when the heart contracts and contracts when the heart expands.

The maps can be used to improve pumping efficiency of the heart. In an efficiently operating heart, each heart segment has an optimal relation between its activation time and the cardiac cycle. Using one of the above described maps, the relationship between the local activation time and the cardiac cycle can be determined. Using a finite-element model of the heart as a pump, underutilized segments of the heart can be determined. The potential for improvement in the heart output can be determined from the model and different methods of improving heart function, such as described below, can be tested.

Figure 11:
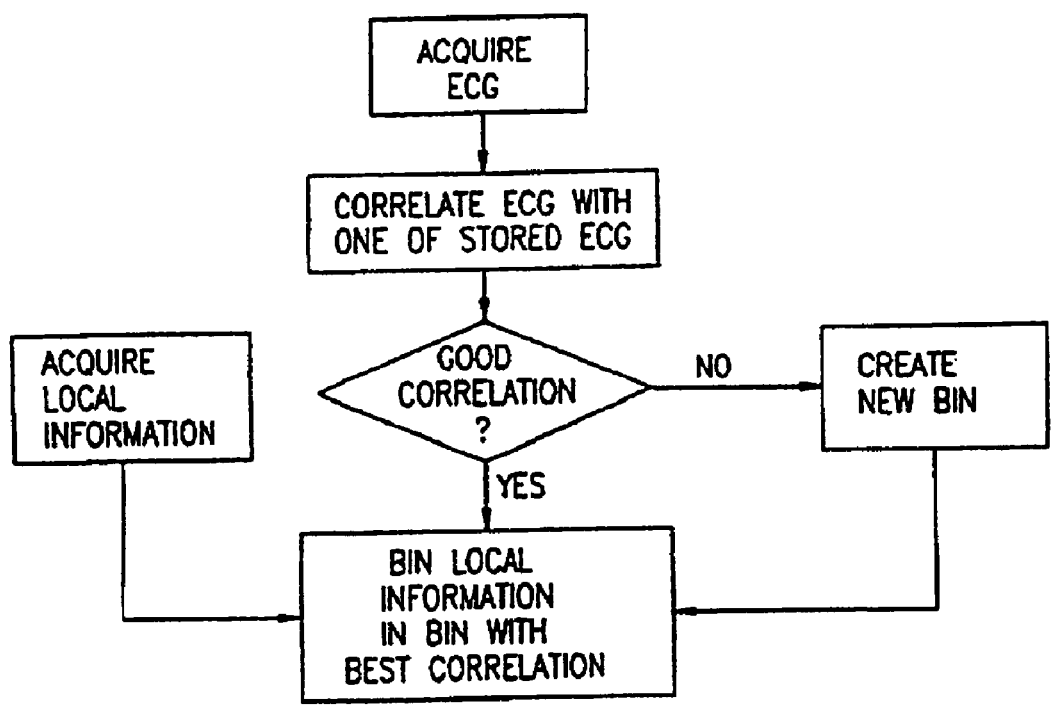
FIG. 11 is a flowchart showing a preferred binning method.

A preferred embodiment of the invention provides a solution to mapping when heart 20 has a non-constant rate. In one case, the heart rate varies, however, it is not arrhythmic. In this case, each heart beat may be treated as one time unit, with an appropriate scaling. Where heart beat is arrhythmic, either naturally, or by choice (manual pacing), position and other sensed values are binned according to ECG or electrogram morphology, beat length, activation location, relative activation time or other determined cardiac parameters. Thus, a plurality of maps may be constructed, each of which corresponds to one bin. FIG. 11 is a flowchart of a preferred binning method. Local information is acquired simultaneously with an associated 12 lead body surface ECG. The morphology of the acquired ECG is correlated with a plurality of stored ECG traces. The local information is stored in a bin which has the highest correlation. Preferably, if the correlation is below a predetermined limit, a new bin is created having the acquired ECG as its associated ECG.

It should be appreciated that locally determined characteristics, such as local electrogram, are associated with a particular segment of heart 20, so that local twisting, moving and contractions can be determined. In many prior art systems, a map of the electrical activity of heart 20 is not associated with specific segments of heart 20 but with general features.

A preferred embodiment of the invention utilizes adaptive mechanisms of the human heart to change the heart, in particular the distribution of muscle mass in the heart.

A general property of muscle tissue, including cardiac muscle, is that muscle tissue hypertrophies in reaction to increased stress and atrophies in reaction to reduced stress. According to a preferred embodiment of the invention, the stress and/or workload in the heart are redistributed to affect the distribution of cardiac muscle mass. Preferably, redistribution of stress and/or workload is achieved by changing the location of pacing in the heart. Muscle tissue that is activated sooner has a longer plateau, and as a result has a longer working time. Muscle which is activated later has a greater initial contractile force (due to its longer initial length caused by the raise in intra-cardiac pressure), but has a shorter plateau and a shorter working time, which mean lower workload. Thus, workload can be redistributed by changing the pacing location.

It should be noted that increasing the plateau duration of a muscle segment can cause both atrophy and hypertrophy of the muscle segment. In general, increasing the plateau duration increases the both the amount of work performed by the muscle segment and the force that the muscle exerts. As a result, the muscle segment may atrophy. However, if the muscle is diseased, the exerted force may not be increased. Further, changing the activation time may reduce the effectiveness of the muscle, so that it hypertrophies, even if the plateau duration was increased. Further, it may be desirable to activate a muscle portion early and/or to extend its activation duration so that better perfused muscle will take over the work of less perfused muscle. Thus, even if the contractile force exerted by the muscle is increased by the increase in plateau duration, this increase is not sufficient to compensate for the increase in workload requirement, with the result that the muscle hypertrophies. Also, since the extent of ionic currents is usually different in healthy and diseased hearts, the effect of changing the plateau duration may be different.

Local uncompensated stress is caused by an increase in intra-cardiac pressure before the muscle is activated (to compensate). In healthy tissue, this stress results in a small amount of stretching, however, in weakened tissue, the stretching may be considerable and cause damage to the muscle. Since changing the pacing affects the amount of local stress which is not compensated for by muscle contraction, stress can also be redistributed by changing the pacing.

Figure 12A:
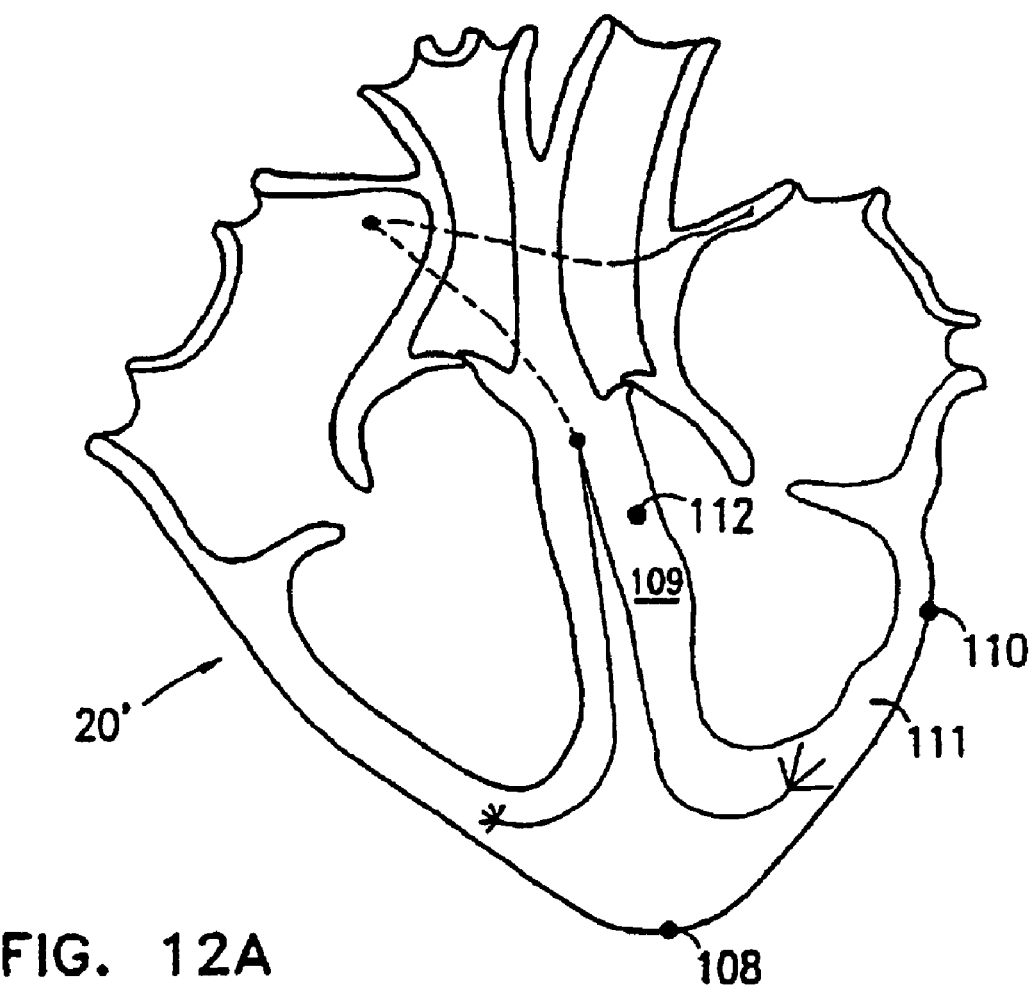
FIGS. 12A–D show pathological cases where a change in pacing of a heart is desirable.

FIG. 12A shows a heart 20' having a hypertrophied ventricular septum 109. The activation of the left ventricle of heart 20' typically starts from a location 108 at the apex of heart 20', with the result that the activation times of a location 110 in an external wall 111 is substantially the same as the activation time of a location 112 in septum 109. If the initial activation location is moved from location 108 to location 112, e.g. by external pacing, septum 109 will be more efficiently utilized, while wall 111 will be activated later in the systole, resulting in a shorter plateau duration of wall 111. As a result, wall 111 will hypertrophy and septum 109 will atrophy, which is a desired result. It should be appreciated, that not all pathological changes in muscle-mass distribution are reversible, especially if slippage of muscle fibers and/or formation of scar tissue are involved.

Figure 12B:
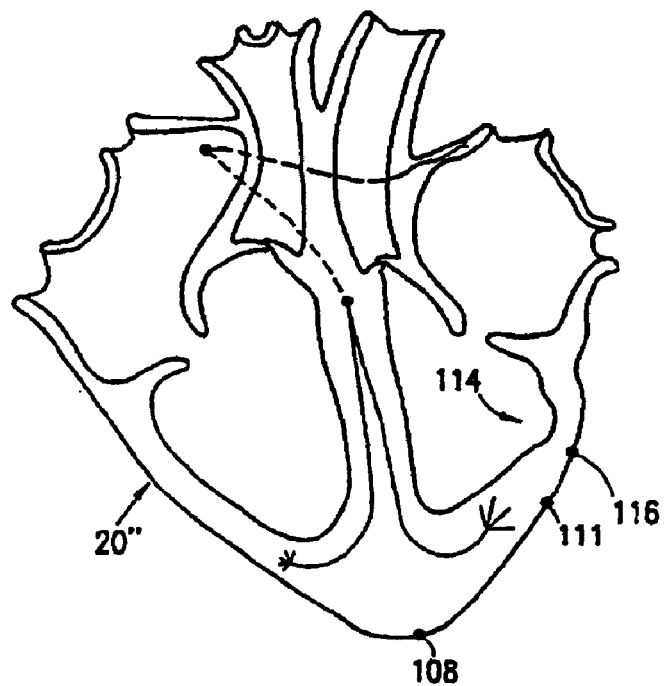

Another preferred embodiment of the invention relates to changing the activation profile of the heart in order to reduce the stress on certain portions of the heart. FIG. 12B shows a heart 20" having a partially infarcted portion 114. Portion 114 has less muscle mass than other parts of wall 111 and, in addition, may be activated later in the cardiac cycle than optimal. As a result, an aneurysm can be expected to form at portion 114. Pacing at location 116, with or without pacing at location 108, both stimulates the existing muscle tissue at portion 114 and, since portion 114 is always contracted when other portions of the left ventricle are contracting, reduces the chances of stretching.

Figure 12C:
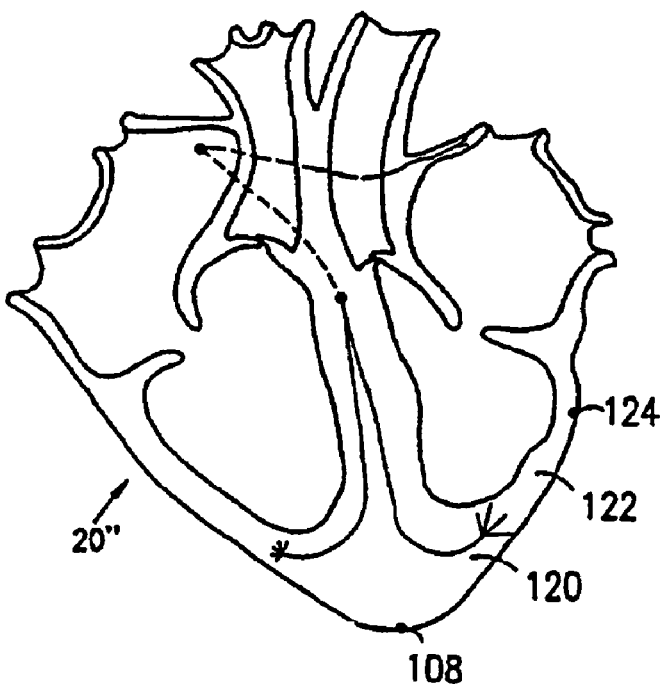

Instead of redistributing stress, other local physiological values can redistributed, for example, a local oxygen requirement. As is well known, the local oxygen requirement is directly related to the local workload. In some diseased hearts, the coronary arteries perfusing a first portion of the heart are more limited in their oxygenation capability than the coronary arteries perfusing a second portion of the heart. In a patient suffering from chronic ischemia in the first portion of the heart, it may be advantageous to redistribute the workload so that the first portion has less workload and the second portion has more workload. FIG. 12C shows heart 20" having a first portion 120 that suffers from chronic ischemia and a second portion 122 that is well oxygenated. If the pacing of the left ventricle of heart 20" is moved from its normal location 108 to a location 124, portion 122 takes over part of the workload of portion 120.

Another type of redistribution relating to perfusion utilizes the fact that the coronary muscle perfuses best during diastole. In a heart having long conduction pathways, some portions may have a very late systole and, as a result, be poorly perfused. In a preferred embodiment of the invention, late activated portions of the heart are paced so that they are activated earlier and, as a result, are better perfused.

As can be appreciated, many physiological values can be redistributed in a more optimal manner by correctly pacing the heart. In particular, local physiological values can be kept within a preferred range by temporal or spatial redistribution. For example, by pacing once from a first location and once from a second location, the average stress at the first location can be equalized to the average stress at the second location.

Another aspect of the present invention relates to optimizing a global parameter of cardiac operation (physiological variable), for example, increasing the cardiac efficiency which ultimately increases the cardiac output and may reduce hypertrophy. The amount of work actually performed by a cardiac muscle segment is dependent on its plateau length (which is dependent on its activation time) and on the correct sequencing of activation of different muscle segments. In an extreme case, a healthy portion of the heart is not activated at all during the cardiac cycle due to a conduction block. In a preferred embodiment of the invention, the output of the heart is increased by changing the activation profile of the heart to better utilize the existing muscle tissue.

Figure 12D:
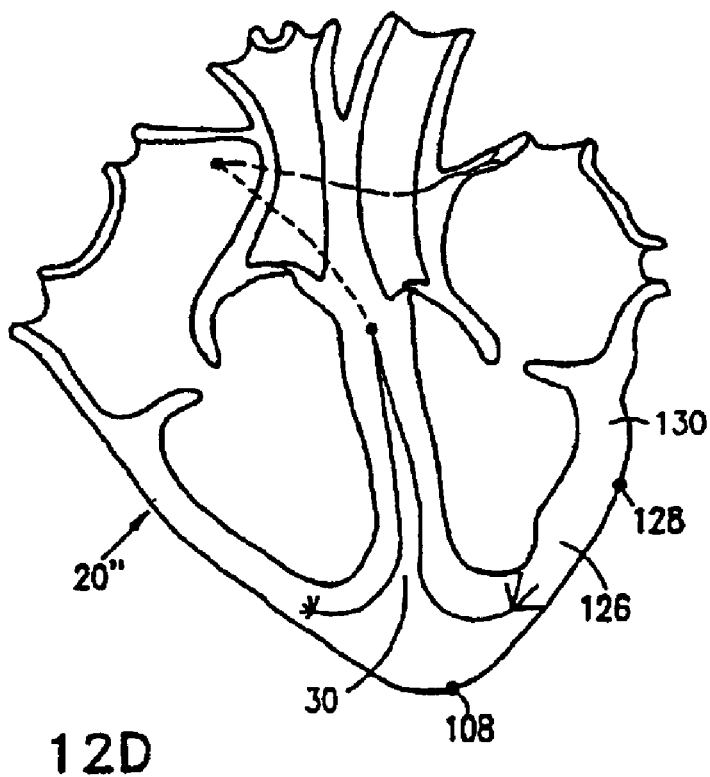

FIG. 12D shows heart 20" having a substantially inactive muscle segment 126 which is closer to natural pacing location 108 of the left ventricle and a healthy muscle segment 130 which is further away from pacing location 108. Muscle segment 130 is not called upon to perform as much work as it can because of its late activation time, on the other hand, segment 126 cannot perform as much work as it should since it is infarcted. Pacing the left ventricle from location 128 transfers the demand from segment 126 to segment 130, which is able to answer the demand. As a result, the output and efficiency of heart 20" increase. If heart 20" hypertrophied to compensate for its reduced output, the hypertrophy may be reversed. Other compensatory mechanisms, such as increased heart rate may also be reversed, resulting in less stress on heart 20".

It should be appreciated that changing the pacing location also affects the utilization of ventricular septum 30. Using a multi-location pacing scheme it is possible to pace at location 128 and simultaneously pace ventricular septum 30, so that it is properly utilized.

Other cardiac physiological variables can also be optimized using the methods of the present invention. For example, by changing the activation profile of the heart, the pressure gradient of the heart can be matched to the impedance of the circulatory system. For example, hypertrophy is an adaptive mechanism for hardening arteries. The increase in size of the left ventricle results in a less pulsile flow which more readily enters the hardened arteries. By changing the activation profile of the heart, the pulse can be made less pulsile without hypertrophy. Other variables which may be optimized include, but are not limited to, heart rate, diastolic interval, long axis and/or short axis shortening, ejection fraction, valvular cross-sectional area, and parameters of the vascular system, such as blood volume and velocity, blood-vessel cross-sectional area and blood pressure. It should be appreciated that such a variable may have a single value or a have a continually changing value whose profile is to be optimized.

In an additional embodiment of the invention, the activation profile of the heart is changed to reduce the maximum intra-cardiac pressure. Although such a reduction typically reduces the heart output, it may be lifesaving in case of an aortic or cardiac aneurysm.

Pacing the heart in the above described embodiments of the invention can be performed in many ways. One pacing method does not require implanting a cardiac pacemaker. Rather, the conduction pathways in the heart are mapped and several of the pathways are disconnected to permanently change the activation profile of the heart. Disconnecting the pathways can be achieved by surgically removing portions of pathways or by ablating those portions, using methods known in the art. Alternatively, new conduction pathways can be formed in the heart, by surgically connecting pathways, by implanting conductive tissues or by implanting electrical conductors. For example, an electrical lead having a distal end and a proximal end, which are both highly conductive, and which can act as a conduction pathway. Optionally, the lead includes a miniature circuitry which charges a capacitor with the plateau voltage from the proximal end and discharges the voltage as an activation signal at the distal end.

Alternatively, a pacemaker can be implanted. Typically, the AV node is ablated and the ventricle is paced as described hereinabove. Alternatively, the AV node is not ablated, the SA node activation signal is sensed and the ventricles are activated artificially before the signal from the AV node arrives at the ventricles. In some embodiments of the invention, such as those explained with reference to FIG. 12B, pacing can proceed in parallel both through the natural pathways and through the artificial ones, with similar beneficial results.

It should be appreciated that the use of multi-electrode pacemakers widens the variety of possible activation profiles and enables a better optimization. In particular, activation times can be more precisely controlled using a multi-electrode pacemaker. Also, the local plateau length can be better controlled when using multi-location pacing.

Another preferred embodiment of the invention provides a pacemaker utilizing one of the above described pacing methods. In such an embodiment, the pacemaker includes sensors for determining the state of global or local cardiac parameters. For example, the intra-cardiac pressure can be monitored, and if it exceeds a certain amount, the pacing regime is changed to effect a change in the activation profile, which in turn affects the intra-cardiac pressure. In another example, the pacemaker measures the stress in certain segments of the heart, and if the stress in one of the segments exceeds a certain limit, the pacing regime is changed so that the stress in the segment is reduced.

In a preferred embodiment of the invention, the pacemaker determines local ischemic conditions, by measuring an injury current. As is known in the art, when the activity of a segment of muscle tissue is impaired, such as by oxygen starvation, the local voltage at rest is higher than in normal muscle. This change in voltage can be directly measured using local sensors. Alternatively, isotonic currents caused by the voltage difference can be measured. Further alternatively, the effect of the voltage changes on an ECG, which are well known in the art, can be utilized to diagnose an ischemic condition.

In an additional embodiment of the invention, the pacing regime is changed so that the stress is temporally redistributed between different segments of the heart. This type of distribution may be required if a high cardiac output is required and most of the heart is chronically ischemic. By cycling the workload, each portion of the heart gets a recuperation period. A temporal redistribution may also be required if it is not possible to efficiently activate two portions of the heart simultaneously, but activation of both is desired so that neither one atrophies as result of non-use.

In a preferred embodiment of the invention, portions of heart 20 are exercised by changing the pacing temporarily to increase the workload, stress or other local values. After a short time, the pacing is returned to a previous regime, which demands less of the exercised portions of heart 20.

There are several ways in which an optimal activation profile and its optimal pacing regime can be determined. In one preferred embodiment of the invention, a map of the heart is constructed and analyzed to determine an optimal activation profile. Such determination is usually performed using a model of the heart, such as a finite-element model. It should be appreciated that a relatively simple map is sufficient in many cases. For example, an activation-time map is sufficient for determining some portions of the heart which are activated too late in the cardiac cycle and are, thus, under utilized. In another example, A map of thickness changes is sufficient to determine portions of the heart which are inactive and/or to detect aneurysms.

Additionally or alternatively, an iterative method is used. A first pacing regime may be determined by analyzing a map or by heuristic methods. After application of the pacing regime, an optimization variable or a distribution of a local variable are measured and the pacing regime changed appropriately. The cycle length of an iteration may be very short, such as for an optimizing pacemaker. In muscle mass redistribution, for example, the determination of the final pacing regime may take longer. First an initial pacing regime is determined for a heart diseased with HCM, after two or three weeks the heart is imaged and the improvement in the condition is determined. Based on the morphological changes in the heart a new pacing regime may be determined. This may be changed a number of times.

A preferred embodiment of the invention relates to optimal placement of pacemaker electrodes. In the past, when a pacemaker is implanted in a heart, the location of the electrodes is determined based on one of the following factors:

(a) the quality and stability of the electrical contact between the electrodes and the heart;

(b) the existence of artifacts in the electrogram; and (c) the effect of the electrode placement and activation timing (for multi-electrode pacemakers) on the heart rhythm.

It should be noted, that since pacemaker electrodes are typically implanted using a fluoroscope, the precision of their placement is low. In a preferred embodiment of the invention, pacemaker electrode placement and/or the pacing regime of the pacemaker are determined such that at least one cardiac parameter or the distribution of local physiological values is optimized, as described above.

In a further preferred embodiment of the invention, an electrode is test-implanted, or simulated by pacing from a catheter, in each of a plurality of electrode locations and the heart output associated with each pacing location is measured. After determining the pacing location which yields the highest cardiac output, the electrode is implanted in that location. Preferably, the electrode is mounted on a position sensing catheter to aid in repositioning of the electrode. Preferably, the catheter comprises a peelable sheath enclosing the electrodes, where the sheath contains at least one position sensor. Further preferably, a steerable catheter is used. Preferably, the operation of the heart is re-evaluated after one or two weeks to determine the effect of the cardiac-adaptation mechanisms on the position of the optimal pacing position. If necessary, one or more electrodes are moved. Alternatively or additionally, when a multi-electrode pacemaker is used, the pacing location can be changed by activating alternative electrodes.

Figure 13:
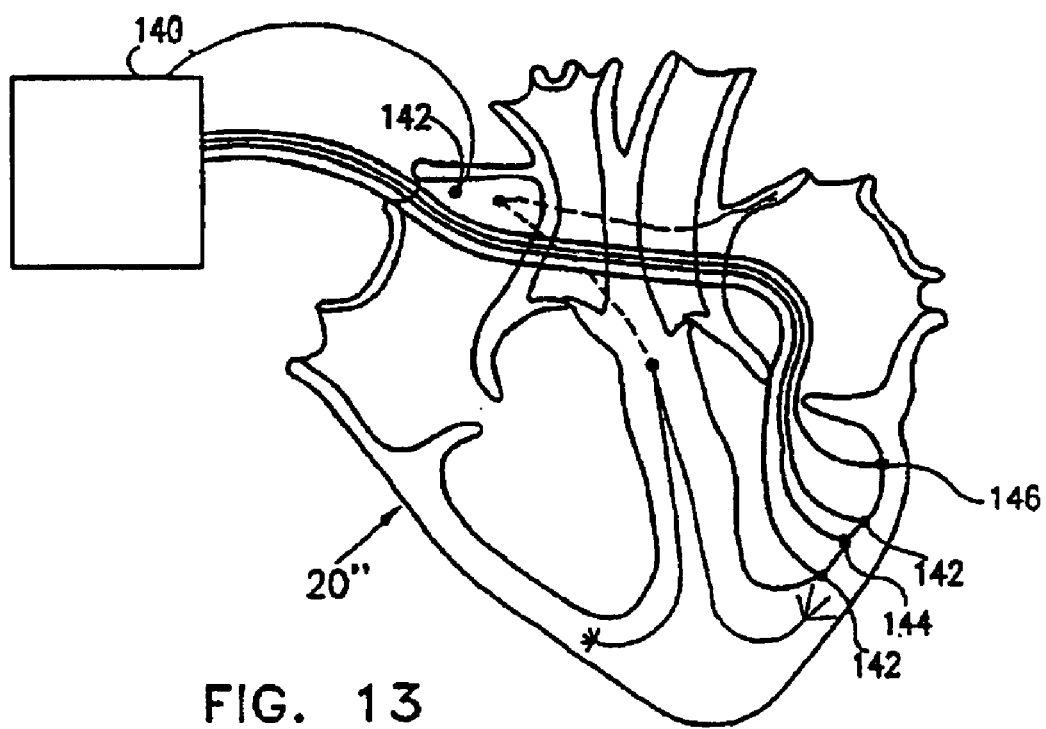
FIG. 13 is a schematic side view of an implanted pacemaker according to a preferred embodiment of the invention.

FIG. 13 shows an implanted pacemaker according to a preferred embodiment of the invention. A control unit 140 electrifies a plurality of electrodes 142 implanted in various locations in heart 20", in accordance with at least one of the pacing regimes described above. Various local physiological values of the heart can be determined using electrodes 142, for example, local activation time and plateau length. Alternatively or additionally, at least one implanted sensor 146 is used to determine local physiological values, such as perfusion and thickness. Alternatively or additionally, a cardiac physiological variable is measured using a sensor 144. Examples of physiological variables include, the intra-cardiac pressure which may be measured using a solid state pressure transducer and the stroke volume, which may be measured using a flow velocity sensor in the aorta. Other variables include: heart rate, diastolic interval, long and short axis shortening, ejection fraction and valvular cross-section. In addition, vascular variables may be measured in any particular vessel, for example, bloodvessel cross-section, vascular flow velocity, vascular flow volume and blood pressure. Any one of these variables can be used to asses the functionality of the heart under a new pacing regime.

It should be appreciated that cardiac mapping can be performed both from the inside of the heart by inserting a catheter into the heart and from the outside of the heart by inserting the catheter into the coronary veins and arteries. Further, mapping, especially electrical mapping, can be performed inside the heart muscle, such as by inserting an electrode carrying needle into the muscle.

Cardiac mapping in accordance with preferred embodiments of the invention, is preferably performed using the Carto system (for electrical mapping) and the Noga system (for electromechanical mapping), both available form Biosense (Israel) Ltd., Tirat HaCarmel, Israel. Some preferred types of mapping catheters are described in a PCT application filed in Israel on Jan. 8, 1997, by applicant "Biosense" and titled "Mapping Catheter", the disclosure of which is incorporated herein by reference.

It should also be appreciated that once the position of the catheter is known, external sensors can be used to provide local physiological values of heart tissue adjacent to the tip of the sensor. For example, if the tip of the catheter caries an ultra-sound marker, an ultrasound image including the marker can be used to determine the local wall thickness. Another example is a combination with SPECT (single photon emission tomography). If the catheter incorporates a radioactive marker suitable for SPECT, local functional information can be gleaned from a SPECT image. Yet another example is determining local perfusion from Doppler-ultrasound images of the coronaries, from nuclear medicine images or from X-ray or CT angiography and overlaying the perfusion map on the geometrical map. In general, a map in accordance with the present invention may be overlaid on or combined with many types of medical data, for example three-dimensional CT data and the like.

One method of aligning an angiogram or a perfusion map with a catheter-acquired map is to acquire both maps substantially simultaneously. The image of the catheter in the perfusion map can then be used to determine if the catheter is near a perfused tissue or nonperfused tissue. Alternatively or additionally, a plurality of reference locations are identified in both the catheter-based map and the perfusion map, so that the two maps can be aligned. The reference locations can be locations either inside or outside the body and they may be identified by placing a position-sensing sensor at the location during the catheter-based mapping. Preferably, the reference locations are also identified during the perfusion mapping by using a position-sensitive sensor, so that the frames of reference for the two maps can be automatically aligned, for example, using the reference catheter as described above. Alternatively or additionally, an appropriate type of radio-opaque or radiative marker is placed on the body so that it is visible during the perfusion mapping. Alternatively, the reference locations are identified from anatomical or functional details in the two maps.

It should be appreciated that a two dimensional angiogram can be aligned, in a clinically useful manner, with a two-dimensional projection of a map of the heart. The appropriate projection direction can be determined from the relative positions of the patient and the angiographic system during the angiography. Preferably, a bi-plane angiogram is aligned with two two-dimensional projections of a map of the heart, alternatively, other types of angiograms or perfusion maps are used. Alignment may be automatic, using fiduciary marks or reference locations as described above. Alternatively, manual alignment or analysis is performed.

It should be appreciated that a catheter can be positioned in almost any part of the body via the vascular system and via body orifices. In addition, a positioning sensing catheter can be surgically inserted in any portion of the body, for example, inserting the catheter into the abdomen or into the thigh. Thus, the above described mapping and pacing (stimulating) methods and apparatus can-also be applied to mapping and stimulating atrophied and injured muscles, mapping the bowels and mapping the electrical and chemical activity of the brain.

The present invention has been described in a plurality of preferred embodiments, each of which has been separately described. It should be appreciated that the present invention contemplates combining various aspects of different embodiments, for example, various types of mappings and various types of pacing may be combined in accordance with preferred embodiments of the invention. Further, many different types of mapable local physiological variables have been described. In various preferred embodiments of the invention, any number of these variables may be mapped and their coupling analyzed to yield information about the activity of a heart. The scope of the invention also includes a pacemaker designed to or programmed to perform any of the above described pacing regimes. Further, the scope of the present invention also encompasses the act of programming a pacemaker to perform any of the above described pacing regimes and the act of modifying pulse parameters in accordance with any embodiment of the present invention. Also, the scope of the invention should be construed to include analyzing such maps, as described herein and apparatus, such as a computer workstation with software, for performing such analyses. In addition the scope of the invention should be construed to include apparatus for acquiring maps as described herein, and in particular software suitable for converting individual local positions, sensed physiological values and electrical activity into such maps. Also such apparatus preferably displays such maps to an operator, either as a snap shot or as a dynamic map.

Another aspect of the present invention relates to computer aided diagnosis. A library of maps representing different types of pathologies, from many patients may be stored on a computer. Since the maps are typically acquired using a computerized system, inputting the maps is easy. When a patient is diagnosed, the diagnosis is stored along with the map, as well as any additional information, such as history, development of the disease, effects of various drugs (with maps to show these effects), effect of new pacing regimes and the like. When a new map is made, this map may be correlated with the maps in the library to more easily diagnose the patient. Maps may be correlated using anatomical landmarks, fiduciary marks inputted by the user, or geometrical alignment. In addition a map may be correlated with a previous map of the same patient to asses the success of a treatment. In a preferred embodiment of the invention, the computer system include an expert system which helps with the diagnosis and/or suggests an appropriate treatment.

It should be appreciated, that even though each person may have a different anatomy and different cardiac disorders, there will be many similarities between maps of different people having similar disorders, such as ischemia due to the blockage of a particular coronary artery.

It will be appreciated by persons skilled in the art that the present invention is not limited to what has thus far been described. Rather the scope of the present invention is limited only by the claims which follow.

What is claimed is:

1. A method for mapping a heart comprising the steps of:
inserting a mapping catheter, having a tip and an ultrasonic position sensor located at the tip, into the heart;
inserting at least one reference catheter having an ultrasonic position sensor into the heart;
placing the tip of the mapping catheter on a surface of the heart at a plurality of points in time of a cardiac cycle;
determining the position of the mapping catheter relative to the at least one reference catheter using the ultrasonic position sensors by making a geometric snapshot of the heart during each point in time of the cardiac cycle; and
mapping the surface of the heart with the mapping catheter and making a map comprised of each geometric snapshot.

2. The method according to claim 1, further comprising mapping electrical activity of a portion of the heart with at least one electrode mounted at the tip of the mapping catheter.

3. The method according to claim 2, further comprising measuring impedance of the portion of the heart.

4. The method according to claim 2, further comprising measuring mechanical information of the portion of the heart.

5. The method according to claim 4, further comprising measuring movement of the portion of the heart.

6. The method according to claim 1, further comprising performing a therapeutic procedure on a portion of the heart.

7. The method according to claim 6, further comprising performing an ablation procedure on the portion of the heart.

8. A method for mapping a heart comprising the steps of:
inserting a mapping catheter, having a tip and an ultrasonic position sensor located at the tip, into the heart;
inserting at least one reference catheter having an ultrasonic position sensor outside of the heart;
placing the tip of the mapping catheter on a surface of the heart at a plurality of points in time of a cardiac cycle;
determining the position of the mapping catheter relative to the at least one reference catheter using the ultrasonic position sensors by making a geometric snapshot of the heart during each point in time of the cardiac cycle; and
mapping the surface of the heart with the mapping catheter and making a map comprised of each geometric snapshot.

9. The method according to claim 8, further comprising mapping electrical activity of a portion of the heart with at least one electrode mounted at the tip of the mapping catheter.

10. The method according to claim 9, further comprising measuring impedance of the portion of the heart.

11. The method according to claim 9, further comprising measuring mechanical information of the portion of the heart.

12. The method according to claim 11, further comprising measuring movement of the portion of the heart.

13. The method according to claim 8, further comprising performing a therapeutic procedure on a portion of the heart.

14. The method according to claim 13, further comprising performing an ablation procedure on the portion of the heart.

15. A method for mapping a heart comprising the steps of:
(a) inserting a mapping catheter, having a tip and an ultrasonic position sensor located at the tip, into the heart;
(b) inserting at least one reference catheter having an ultrasonic position sensor into the heart;
(c) bringing the tip of the mapping catheter into contact with a wall of the heart at a location at a point in time of a cardiac cycle;
(d) determining a position of the tip of the mapping catheter at the location using the ultrasonic position sensors and making a geometric snapshot of the wall of the heart;
(e) moving the tip of the mapping catheter to a second location at another point in time of the cardiac cycle and making a second geometric snapshot of the wall of the heart; and
(f) making a map of the wall of the heart based on the geometric snapshots by repeating steps (d)–(e).

16. The method according to claim 15, further comprising mapping electrical activity of a surface of the heart with at least one electrode mounted at the tip of the mapping catheter.

17. The method according to claim 16, further comprising measuring impedance of the surface of the heart.

18. The method according to claim 15, further comprising performing a therapeutic procedure on a surface of the heart.

19. The method according to claim 18, further comprising performing an ablation procedure on the surface of the heart.

20. The method according to claim 15, further comprising measuring mechanical information of a surface of the heart.

21. The method according to claim 20, further comprising measuring movement of the surface of the heart.

22. A method for mapping a heart comprising the steps of:
(a) inserting a mapping catheter, having a tip and an ultrasonic position sensor located at the tip, into the heart;
(b) inserting at least one reference catheter having an ultrasonic position sensor outside of the heart;
(c) bringing the tip of the mapping catheter into contact with a wall of the heart at a location at a point in time of a cardiac cycle;
(d) determining a position of the tip of the mapping catheter at the location using the ultrasonic position sensors and making a geometric snapshot of the wall of the heart;
(e) moving the tip of the mapping catheter to a second location at another point in time of the cardiac cycle and making a second geometric snapshot of the wall of the heart; and
(f) making a map of the wall of the heart based on the geometric snapshots by repeating steps (d)–(e).

23. The method according to claim 22, further comprising mapping electrical activity of a surface of the heart with at least one electrode mounted at the tip of the mapping catheter.

24. The method according to claim 23, further comprising measuring impedance of the surface of the heart.

25. The method according to claim 22, further comprising performing a therapeutic procedure on a surface of the heart.

26. The method according to claim 25, further comprising performing an ablation procedure on the surface of the heart.

27. The method according to claim 22, further comprising measuring mechanical information of a surface of the heart.

28. The method according to claim 27, further comprising measuring movement of the surface of the heart.

* * * * *